(12) United States Patent
Funahashi

(10) Patent No.: US 7,586,006 B2
(45) Date of Patent: Sep. 8, 2009

(54) AROMATIC AMINE DERIVATIVE AND ORGANIC ELECTROLUMINESCENT ELEMENT EMPLOYING THE SAME

(75) Inventor: Masakazu Funahashi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 93 days.

(21) Appl. No.: 10/552,449

(22) PCT Filed: Jan. 13, 2004

(86) PCT No.: PCT/JP2004/000140

§ 371 (c)(1),
(2), (4) Date: Nov. 10, 2005

(87) PCT Pub. No.: WO2004/092111

PCT Pub. Date: Oct. 28, 2004

(65) Prior Publication Data

US 2006/0202190 A1  Sep. 14, 2006

(30) Foreign Application Priority Data

Apr. 10, 2003 (JP) .............................. 2003-106231

(51) Int. Cl.
*C07C 211/00* (2006.01)
*H05B 33/14* (2006.01)
(52) U.S. Cl. ...................... 564/427; 564/308; 428/690; 428/704; 428/917
(58) Field of Classification Search ................. 564/308, 564/427; 428/690, 704, 917
See application file for complete search history.

(56) References Cited

U.S. PATENT DOCUMENTS 5,759,444 A * 6/1998 Enokida et al. ........ 252/301.16
6,251,531 B1   6/2001 Enokida et al.
2003/0069443 A1 * 4/2003 Kamikawa et al. .......... 562/405

FOREIGN PATENT DOCUMENTS

| EP | 0 765 106 A2 | 3/1997 |
|----|----|----|
| EP | 1 541 657 | 6/2005 |
| JP | 03-200889 | 9/1991 |
| JP | 07-138561 | 5/1995 |
| JP | 08-239655 | 9/1996 |
| JP | 2001-207167 | 7/2001 |

OTHER PUBLICATIONS

C.W. Tang, et al., "Organic Electroluminescent Diodes," *Appl. Phys. Lett.*, vol. 51, No. 12, Sep. 21, 1987, pp. 913-915.

* cited by examiner

*Primary Examiner*—Shailendra Kumar
(74) *Attorney, Agent, or Firm*—Steptoe & Johnson LLP

(57) ABSTRACT

The present invention relates to aromatic amine derivatives having a specific structure in which a substituted anthracene structure is bonded to an amine structure substituted with benzene rings having substituent groups; and organic electroluminescence devices comprising a cathode, an anode and one or plural organic thin film layers having at least a light emitting layer which are sandwiched between the cathode and the anode wherein at least one of the organic thin film layers contains the above aromatic amine derivative in the form of a single substance or a component of a mixture. There are provided organic electroluminescence devices having a high luminance of light emitted and a high efficiency of blue light emission and exhibiting a long life, as well as novel aromatic amine derivatives capable of realizing such organic electroluminescence devices.

9 Claims, 6 Drawing Sheets

AROMATIC AMINE DERIVATIVE AND ORGANIC ELECTROLUMINESCENT ELEMENT EMPLOYING THE SAME

This application is a 371 of PCT/JP04/00140, filed Jan. 13, 2004.

TECHNICAL FIELD

The present invention relates to novel aromatic amine derivatives and organic electroluminescence devices using the same, and more particularly to organic electroluminescence devices which exhibit a high luminance of light emitted and a high efficiency of light emission and have a long life, and novel aromatic amine derivatives capable of realizing such organic electroluminescence devices.

BACKGROUND ART

The organic electroluminescence devices (organic EL devices) are spontaneous light emitting devices which utilize the principle that a fluorescent substance emits light by energy of recombination between holes injected from an anode and electrons injected from a cathode upon application of an electric field thereto.

Since C. W. Tang, et al., of Eastman Kodak Company have reported organic EL devices of a laminate type driven at a low electric voltage (C. W. Tang and S. A. Vanslyke, "Applied Physics Letters", Vol. 51, p. 913, 1987, etc.), many studies have been intensely conducted on organic EL devices made of organic materials.

The organic EL devices reported by Tang, et al., have such a laminate structure including a light emitting layer made of tris(8-hydroxyquinolinol)aluminum and a hole transport layer made of a triphenyl diamine derivative. The laminate structure of these devices has advantages such as increased efficiency of hole injection into the light emitting layer, increased efficiency of production of excited particles (excitons) which are produced by blocking electrons injected from a cathode and recombining the electrons with holes, and confinement of the excitons produced within the light emitting layer. As the structure of such organic EL devices, there are well known a two-layer structure including a hole transporting (injecting) layer and an electron transporting and light emitting layer, a three-layer structure including a hole transporting (injecting) layer, a light emitting layer and an electron transporting (injecting) layer, etc. In these organic EL devices of a laminate type, various structures and production methods thereof have been proposed in order to enhance an efficiency of recombination between holes and electrons injected thereinto.

As the light emitting materials for the organic EL devices, there are known chelate complexes such as tris(8-quinolinolato)aluminum complexes, coumarin derivatives, tetraphenyl butadiene derivatives, bis-styryl arylene derivatives and oxadiazole derivatives. It has been reported that these light emitting materials emit blue to red light in a visible range, and it is therefore expected to realize color display devices by using these light emitting materials (for example, refer to JP 8-239655A, JP 7-138561A and JP 3-200889A, etc.).

In addition, JP 2001-207167A discloses the devices using aminoanthracene derivatives as a green light emitting material. However, the light emitting material has failed to provide devices having a long life and a high efficiency of light emission and, therefore, has been practically unusable.

In recent years, although many organic EL devices having a high luminance and a long life have been disclosed or reported, the performance thereof has been still unsatisfactory. Therefore, is has been strongly demanded to develop materials for organic EL devices having a more excellent efficiency of light emission.

DISCLOSURE OF THE INVENTION

The present invention has been made to solve the above problems. An object of the present invention is to provide organic EL devices which exhibit a high luminance of light emitted and a high efficiency of light emission and have a long life, and novel aromatic amine derivatives capable of realizing such organic EL devices.

As a result of extensive researches for developing materials for organic EL devices having the above advantageous properties as well as organic EL devices using such materials, the inventors have found that the above object can be achieved by using aromatic amine derivatives represented by the following general formula (1) in which a substituted anthracene structure is bonded to an amine structure substituted with benzene rings having substituent groups. The present invention has been accomplished on the basis of the above finding.

Thus, the present invention provides:

An aromatic amine derivative represented by the following general formula (1):

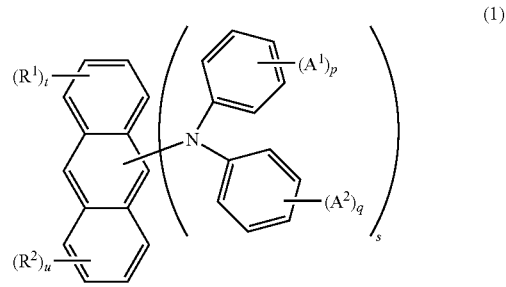

wherein $A^1$ and $A^2$ are each independently a hydrogen atom, a substituted or unsubstituted alkyl group having 1 to 10 carbon atoms, a substituted or unsubstituted aryl group having 5 to 50 nuclear carbon atoms, a substituted or unsubstituted cycloalkyl group having 3 to 20 nuclear carbon atoms, a substituted or unsubstituted alkoxy group having 1 to 10 carbon atoms, a substituted or unsubstituted aryloxy group having 5 to 50 nuclear carbon atoms, a substituted or unsubstituted arylamino group having 5 to 50 nuclear carbon atoms, a substituted or unsubstituted alkylamino group having 1 to 10 carbon atoms, or a halogen atom; p and q are each an integer of 1 to 5 and s is an integer of 1 to 9 wherein when p or q is 2 or more, a plurality of $A^1$ or $A^2$ groups may be the same or different and may be bonded to each other to form an saturated or unsaturated ring, with the proviso that both of $A^1$ and $A^2$ are not simultaneously hydrogen atoms;

$R^1$ is a substituted or unsubstituted secondary or tertiary alkyl group having 3 to 10 carbon atoms, or a substituted or unsubstituted secondary or tertiary cycloalkyl group having 3 to 10 carbon atoms; t is an integer of 1 to 9, and when t is 2 or more, a plurality of $R^1$ groups may be the same or different;

$R^2$ is a hydrogen atom, a substituted or unsubstituted alkyl group having 1 to 10 carbon atoms, a substituted or unsubstituted aryl group having 5 to 50 nuclear carbon atoms, a substituted or unsubstituted cycloalkyl group having 3 to 20 nuclear carbon atoms, a substituted or unsubstituted alkoxy group having 1 to 10 carbon atoms, a substituted or unsubstituted aryloxy group having 5 to 50 nuclear carbon atoms, a substituted or unsubstituted arylamino group having 5 to 50 nuclear carbon atoms, a substituted or unsubstituted alkylamino group having 1 to 10 carbon atoms, or a halogen atom; u is an integer of 0 to 8 and when u is 2 or more, a plurality of $R^2$ groups may be the same or different; and a sum of s, t and u (s+t+u) is an integer of 2 to 10.

Also, the present invention provides:

An organic electroluminescence device comprising a cathode, an anode and one or plural organic thin film layers having at least a light emitting layer which are sandwiched between the cathode and the anode, wherein at least one of the organic thin film layers contains the above aromatic amine derivative in the form of a single substance or a component of a mixture. The light emitting layer preferably contains the aromatic amine derivative in the form of a single substance or a component of a mixture.

BEST MODE FOR CARRYING OUT THE INVENTION

Figure 1:
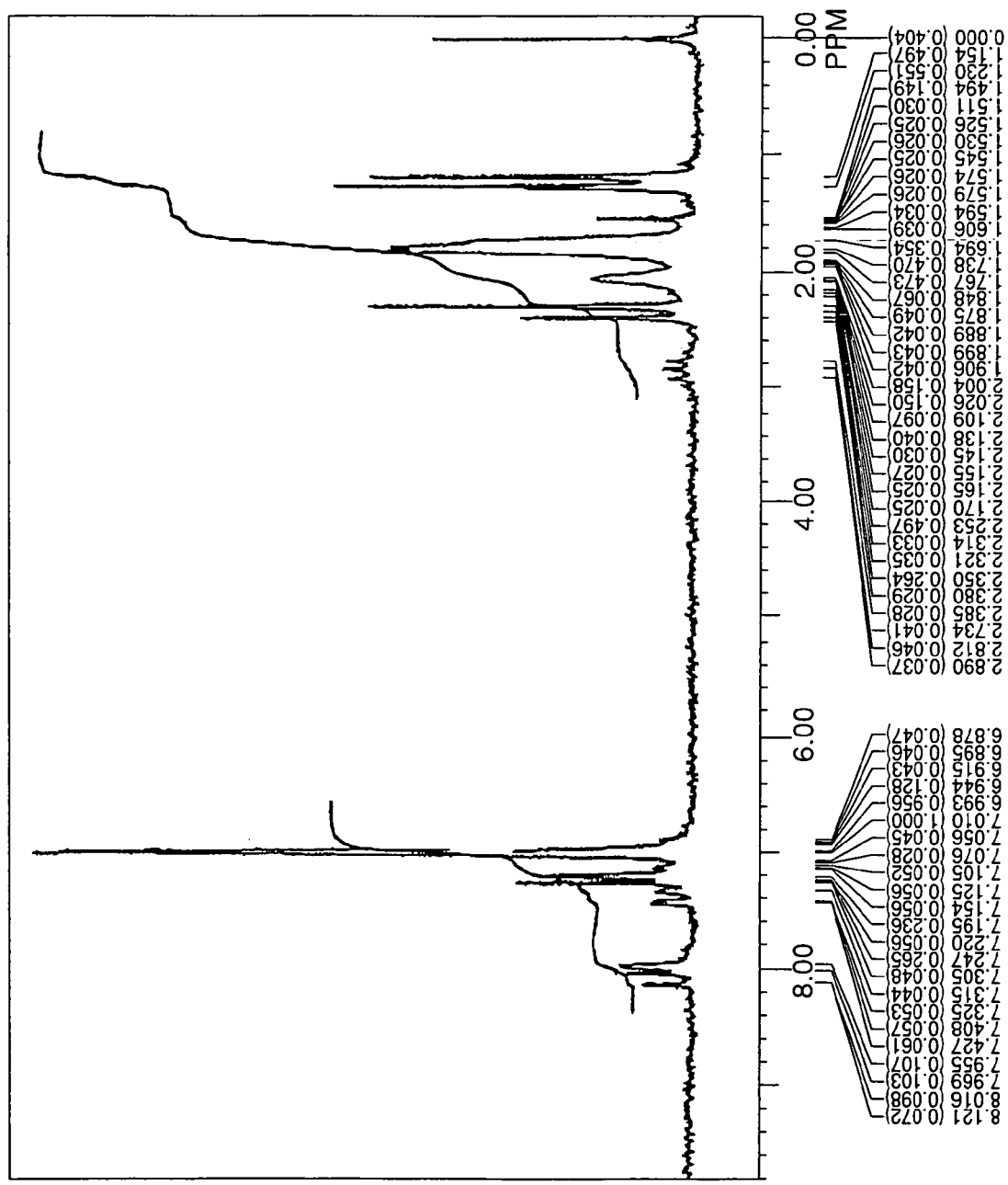
FIG. 1 is a view showing NMR spectrum of the compound (6) as an example of the aromatic amine derivatives of the present invention.

The novel aromatic amine derivatives of the present invention are represented by the following general formula (1):

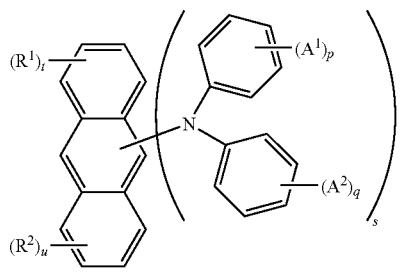

(1)

In the general formula (1), $A^1$ and $A^2$ are each independently a hydrogen atom; a substituted or unsubstituted alkyl group having 1 to 10 carbon atoms and preferably 1 to 6 carbon atoms; a substituted or unsubstituted aryl group having 5 to 50 nuclear carbon atoms and preferably 5 to 10 nuclear carbon atoms; a substituted or unsubstituted cycloalkyl group having 3 to 20 nuclear carbon atoms and preferably 5 to 10 nuclear carbon atoms; a substituted or unsubstituted alkoxy group having 1 to 10 carbon atoms and preferably 1 to 6 carbon atoms; a substituted or unsubstituted aryloxy group having 5 to 50 nuclear carbon atoms and preferably 5 to 10 nuclear carbon atoms; a substituted or unsubstituted arylamino group having 5 to 50 nuclear carbon atoms and preferably 5 to 20 nuclear carbon atoms; a substituted or unsubstituted alkylamino group having 1 to 10 carbon atoms and preferably 1 to 6 carbon atoms; or a halogen atom.

Examples of the substituted or unsubstituted alkyl group as $A^1$ and $A^2$ include methyl, ethyl, propyl, isopropyl, butyl, sec-butyl, tert-butyl, pentyl, hexyl, heptyl, octyl, stearyl, 2-phenylisopropyl, trichloromethyl, trifluoromethyl, benzyl, α-phenoxybenzyl, α,α-dimethylbenzyl, α,α-methylphenylbenzyl, α,α-ditrifluoromethylbenzyl, triphneylmethyl and α-benzyloxybenzyl.

Examples of the substituted or unsubstituted aryl group as $A^1$ and $A^2$ include phenyl, 2-methylphenyl, 3-methylphenyl, 4-methylphenyl, 4-ethylphenyl, biphenyl, 4-methyl biphenyl, 4-ethyl biphenyl, 4-cyclohexyl biphenyl, terphenyl, 3,5-dichlorophenyl, naphthyl, 5-methyl naphthyl, anthryl and pyrenyl.

Examples of the substituted or unsubstituted cycloalkyl group as $A^1$ and $A^2$ include cyclopropyl, cyclobutyl, cyclopentyl, cyclohexyl, norbornyl and adamantyl.

Examples of the substituted or unsubstituted alkoxy group as $A^1$ and $A^2$ include methoxy, ethoxy, propoxy, isopropoxy, butoxy, isobutoxy, sec-butoxy, tert-butoxy, various pentyloxy groups and various hexyloxy groups.

Examples of the substituted or unsubstituted aryloxy group as $A^1$ and $A^2$ include phenoxy, tolyloxy and naphthyloxy.

Examples of the substituted or unsubstituted arylamino group as $A^1$ and $A^2$ include diphenylamino, ditolylamino, dinaphthylamino and naphthylphenylamino.

Examples of the substituted or unsubstituted alkylamino group as $A^1$ and $A^2$ include dimethylamino, diethylamino and dihexylamino.

Examples of the halogen atom as $A^1$ and $A^2$ include a fluorine atom, a chlorine atom, a bromine atom, etc.

However, in the general formula (1), both of $A^1$ and $A^2$ are not simultaneously hydrogen atoms.

In the general formula (1), $A^1$ is preferably a secondary or tertiary alkyl group or a secondary or tertiary cycloalkyl group, and more preferably a secondary alkyl group or a secondary cycloalkyl group, and $A^2$ is preferably a primary or secondary alkyl group, and more preferably methyl, ethyl, propyl, isopropyl, butyl, sec-butyl or tert-butyl.

In the general formula (1), p and q are each an integer of 1 to 5 and preferably 1 to 3. More preferably, p is 1 and q is 1 or 2.

When p or q is 2 or more, a plurality of $A^1$ or $A^2$ groups may be the same or different and may be bonded to each other to form an saturated or unsaturated ring.

Also, s is an integer of 1 to 9 and preferably 1 to 3.

$R^1$ is a substituted or unsubstituted secondary or tertiary alkyl group having 3 to 10 carbon atoms, or a substituted or unsubstituted secondary or tertiary cycloalkyl group having 3 to 10 carbon atoms.

Examples of the substituted or unsubstituted secondary or tertiary alkyl group as $R^1$ include isopropyl, tert-butyl, sec-butyl, tert-pentyl, 1-methylbutyl, 1-methylpentyl, 1,1'-dimethylpentyl, 1,1'-diethylpropyl, 1-benzyl-2-phenylethyl, 1-methoxyethyl and 1-phenyl-1-methylethyl.

Examples of the substituted or unsubstituted secondary or tertiary cycloalkyl group as $R^1$ include cyclopentyl, norbornyl and adamantyl.

In the general formula (1), $R^1$ is preferably a tertiary alkyl group or a secondary cycloalkyl group, more preferably tert-butyl or cyclohexyl, and most preferably cyclohexyl.

In the general formula (1), t is an integer of 1 to 9 and preferably 1 to 3. When t is 2 or more, a plurality of $R^1$ groups may be the same or different.

$R^2$ is a hydrogen atom, a substituted or unsubstituted alkyl group having 1 to 10 carbon atoms and preferably 1 to 6 carbon atoms; a substituted or unsubstituted aryl group having 5 to 50 nuclear carbon atoms and preferably 5 to 10 nuclear carbon atoms; a substituted or unsubstituted cycloalkyl group having 3 to 20 nuclear carbon atoms and preferably 5 to 10 nuclear carbon atoms; a substituted or unsubstituted alkoxy group having 1 to 10 carbon atoms and preferably 1 to 6 carbon atoms; a substituted or unsubstituted aryloxy group having 5 to 50 nuclear carbon atoms and preferably 5 to 10 nuclear carbon atoms; a substituted or unsubstituted arylamino group having 5 to 50 nuclear carbon atoms and preferably 5 to 20 nuclear carbon atoms; a substituted or unsubstituted alkylamino group having 1 to 10 carbon atoms and preferably 1 to 6 carbon atoms; or a halogen atom.

Specific examples of the substituted or unsubstituted alkyl, aryl, cycloalkyl, alkoxy, aryloxy, arylamino and alkylamino groups as well as the halogen atom as $R^2$ include the same groups as those exemplified as $A^1$ and $A^2$ above.

In the general formula (1), $R^2$ is preferably a tertiary alkyl group or a secondary cycloalkyl group, more preferably tert-butyl or cyclohexyl, and most preferably cyclohexyl.

In the general formula (1), u is an integer of 0 to 8 and preferably 0 to 2. When u is 2 or more, a plurality of $R^2$ groups may be the same or different.

Also, in the general formula (1), a sum of s, t and u (s+t+u) is an integer of 2 to 10 and preferably 2 to 6.

Further, the aromatic amine derivatives having the structure represented by the general formula (1) according to the present invention are preferably any of the compounds represented by the following general formulae (2), (2-1) to (2-3) and (3) to (5):

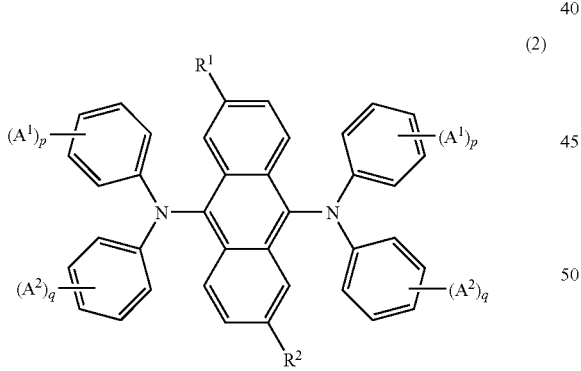
(2)

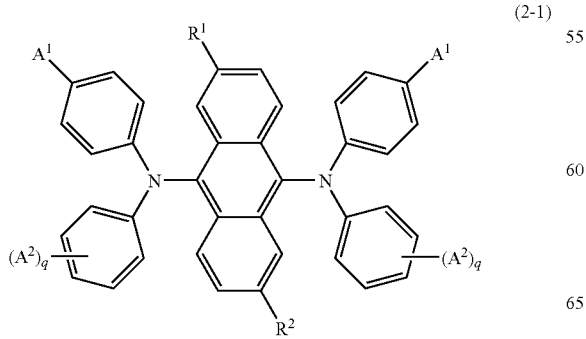
(2-1)

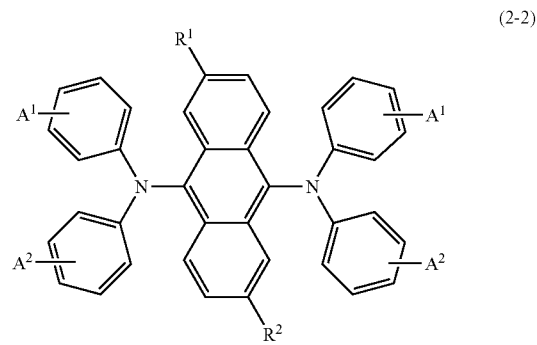
(2-2)

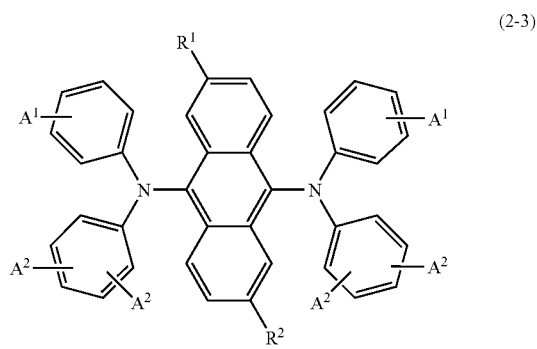
(2-3)

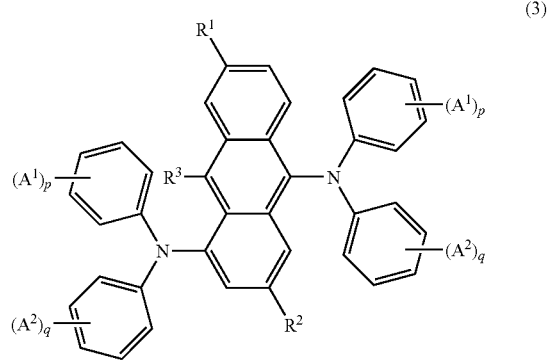
(3)

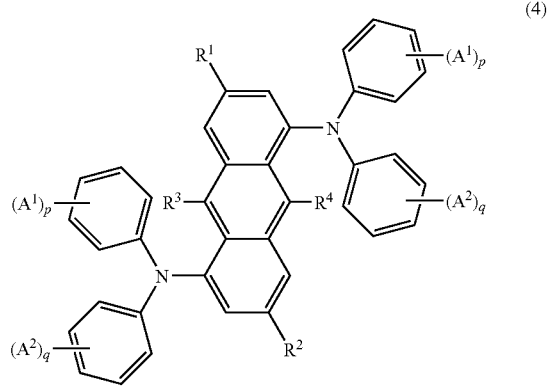
(4)

-continued

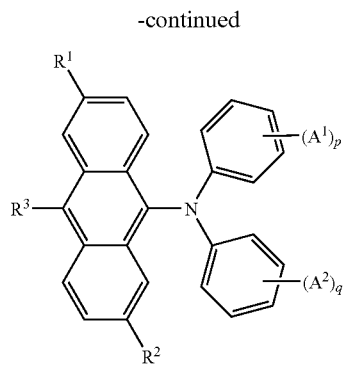

(5)

In the general formulae (2), (2-1) to (2-3) and (3) to (5), $A^1, A^2$, p, q, $R^1$ and $R^2$ are the same as defined above. Also, $R^3$ and $R^4$ are respectively the same as $R^2$, and examples of the preferred $R^3$ and $R^4$ are also the same as those of $R^2$.

Specific examples of the aromatic amine derivatives represented by the general formulae (1) as well as (2), (2-1) to (2-3) and (3) to (5) include compounds (1) to (65) enumerated below, though not particularly limited thereto. Meanwhile, in the following compounds, Me represents a methyl group.

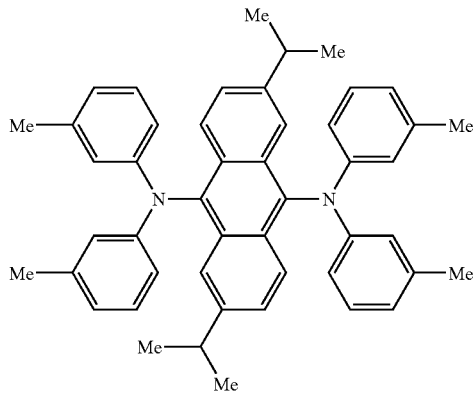

(1)

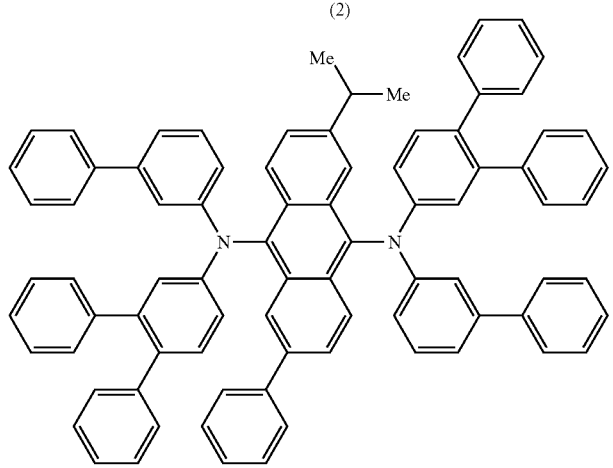

(2)

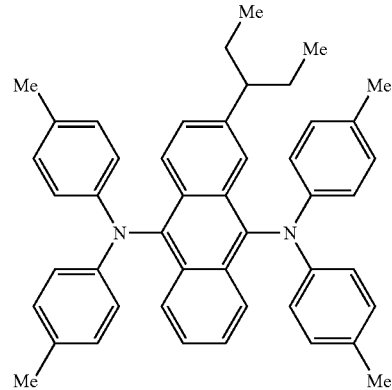

(3)

(4)
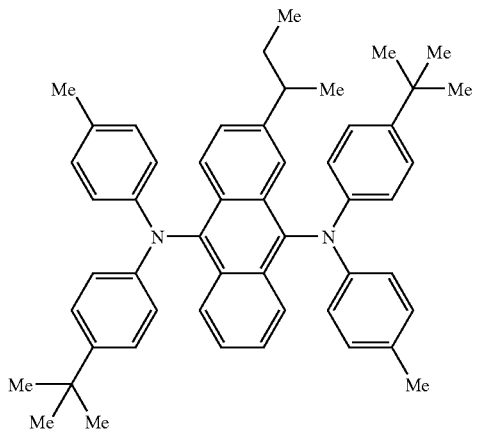
(5)
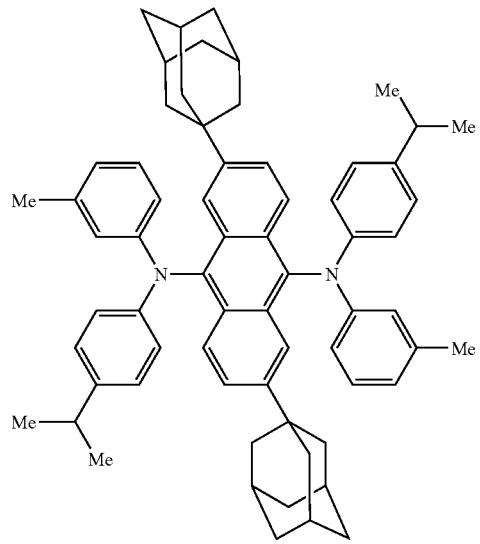
(6)
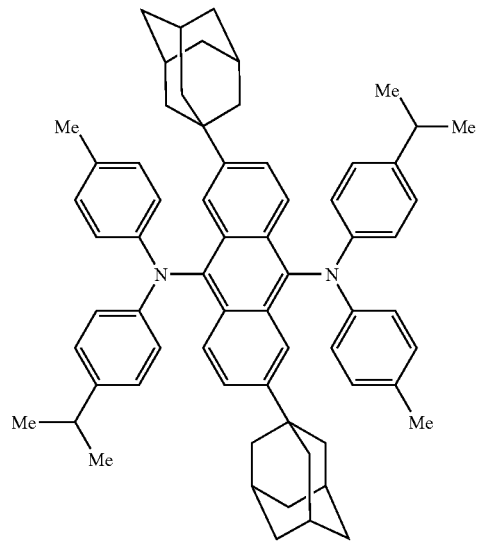

-continued
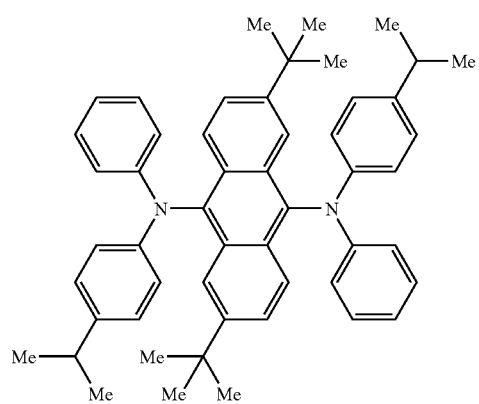
(7)
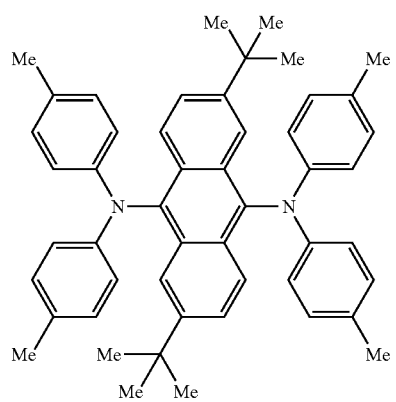
(8)
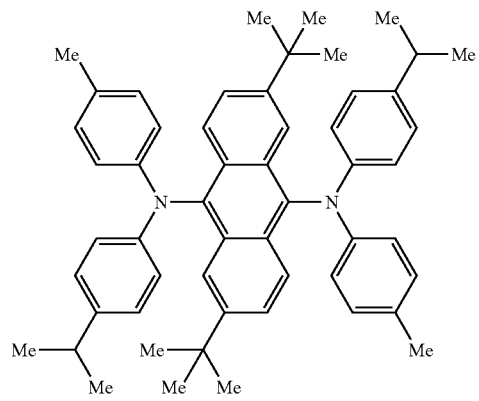
(9)
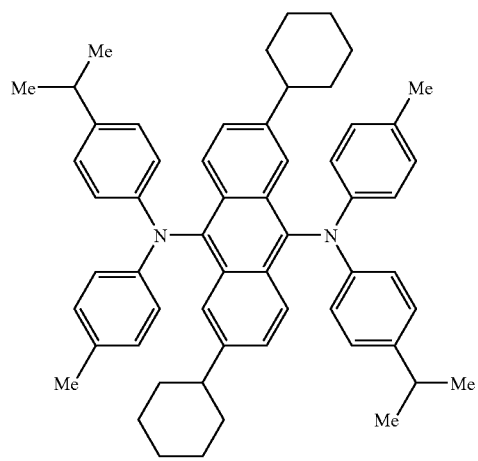
(10)

-continued
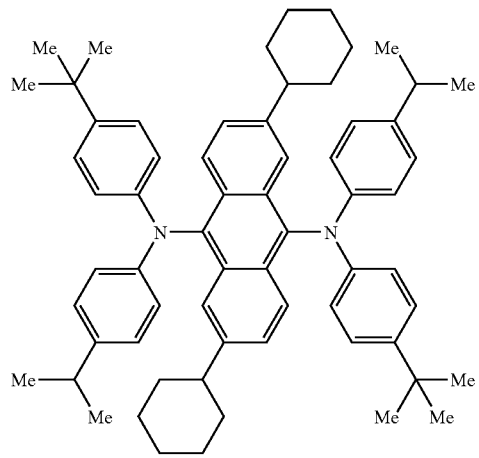
(11)
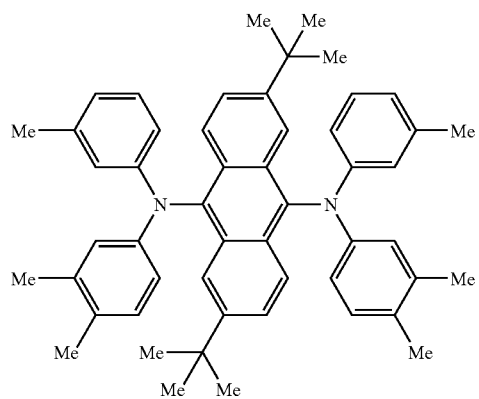
(12)
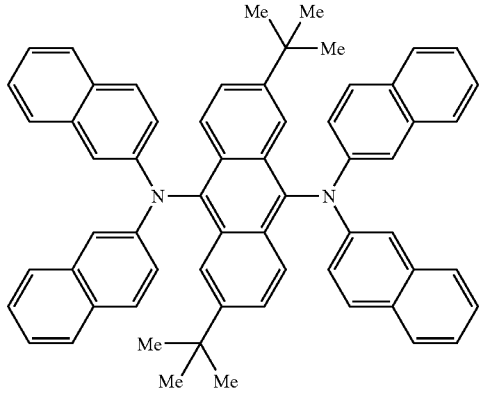
(13)
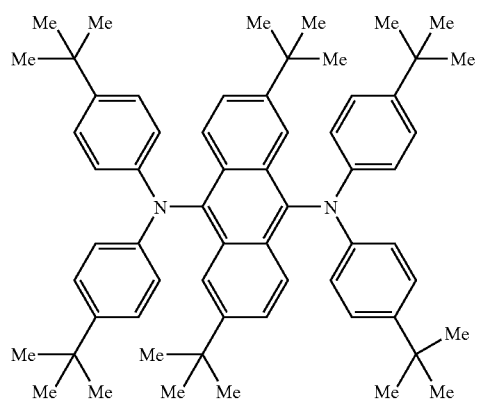
(14)

-continued
(15)
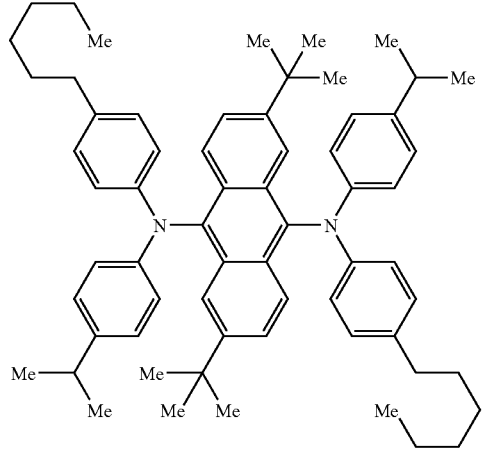
(16)
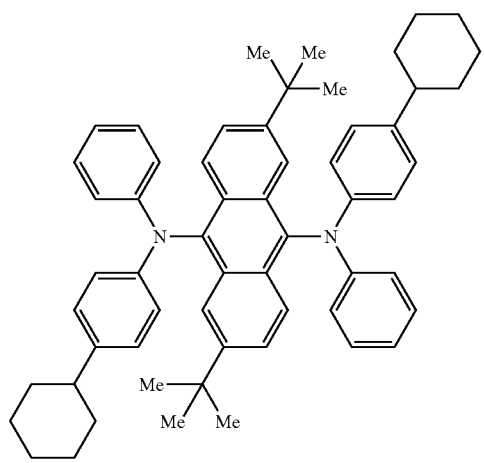
(17)
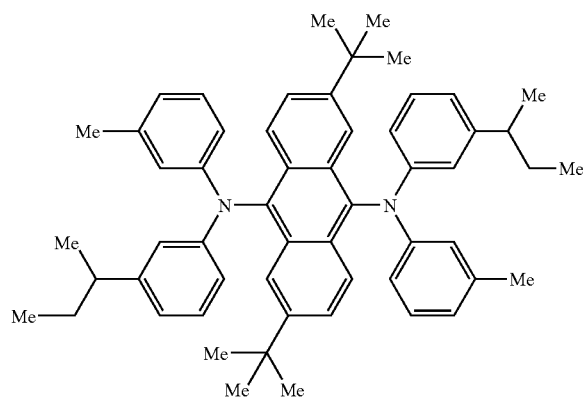

(18)
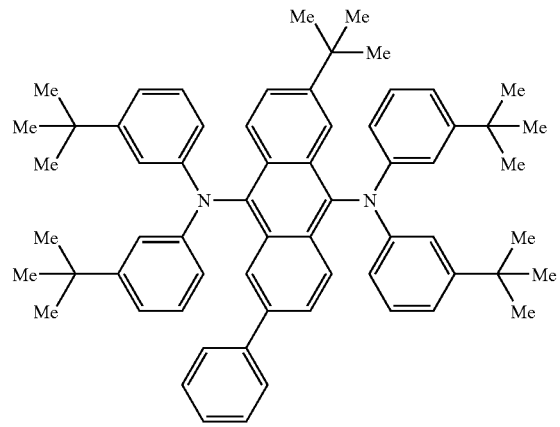
(19)
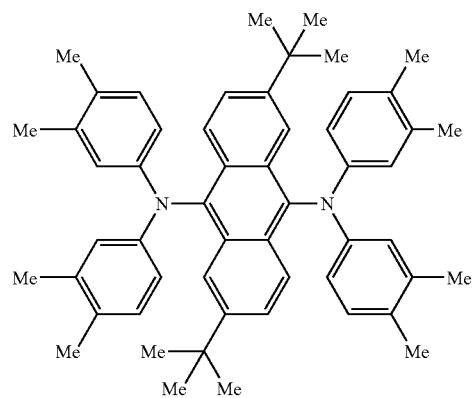
(20)
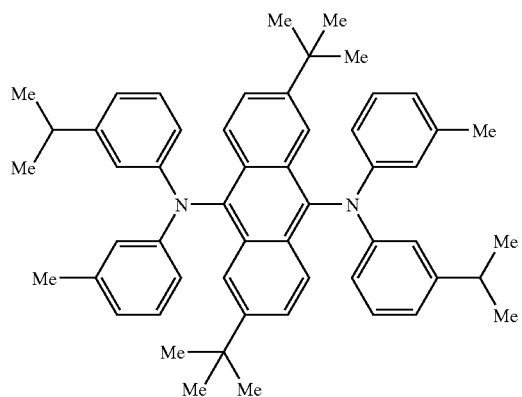

-continued
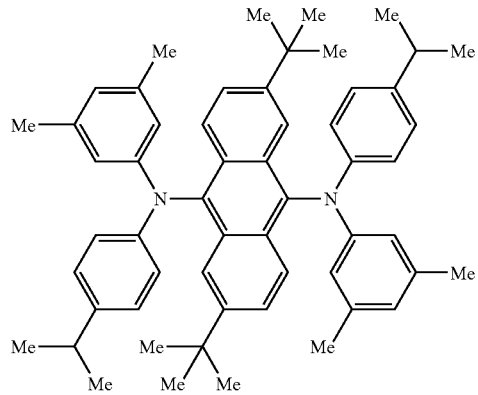
(21)
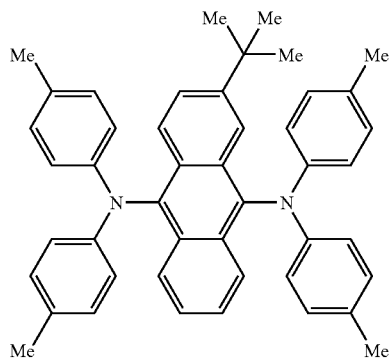
(22)
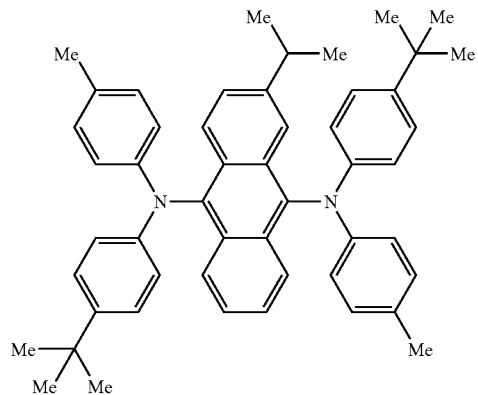
(23)
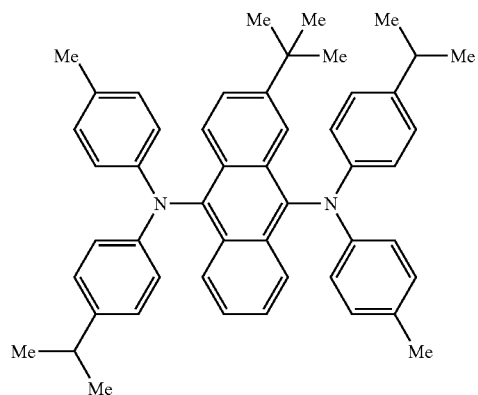
(24)

-continued
(25)
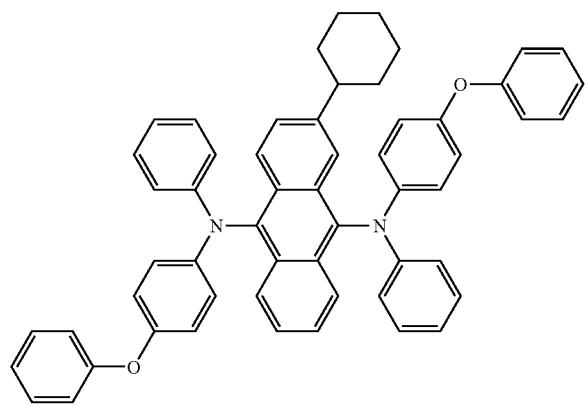
(26)
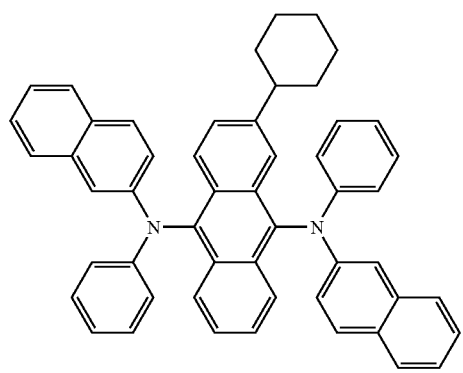
(27)
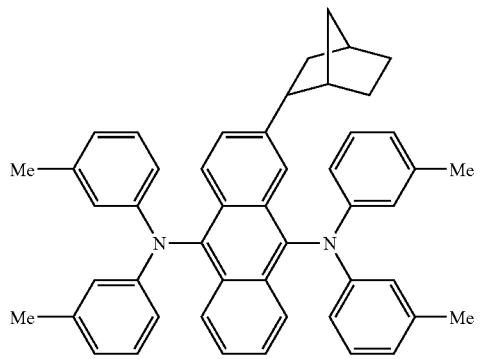
(28)
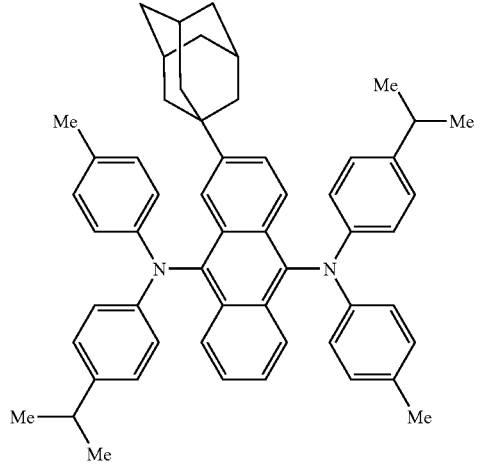

-continued
(29)
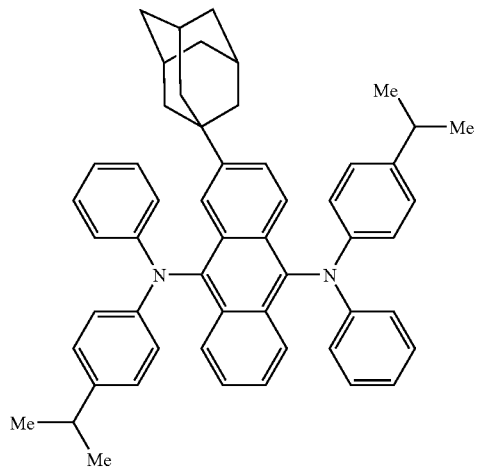
(30)
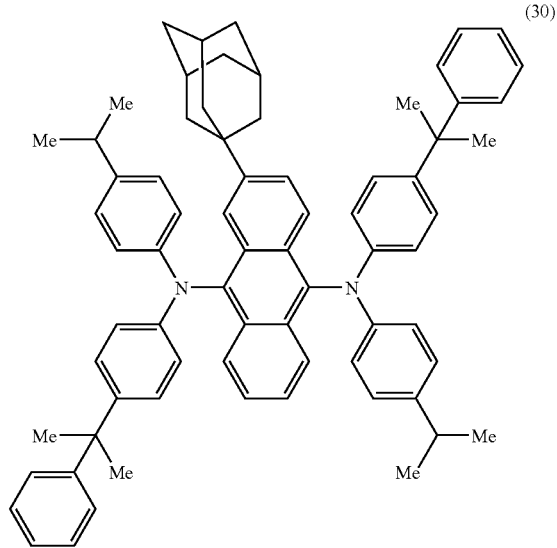
(31)
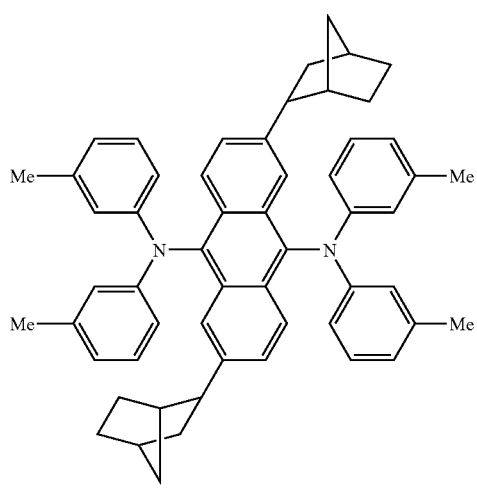

-continued
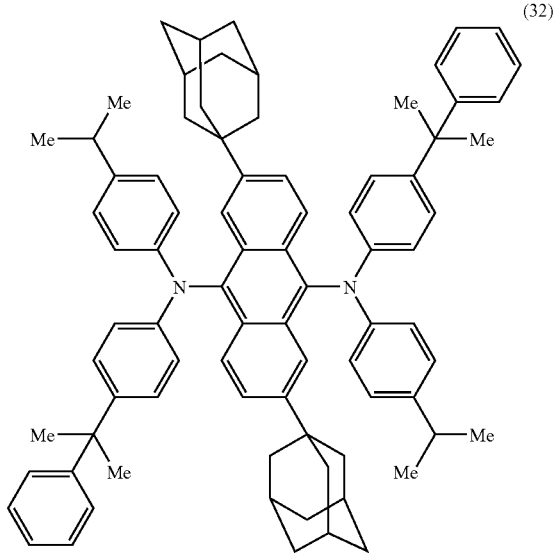
(32)
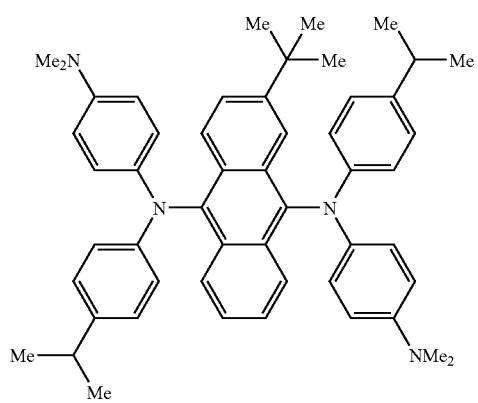
(33)
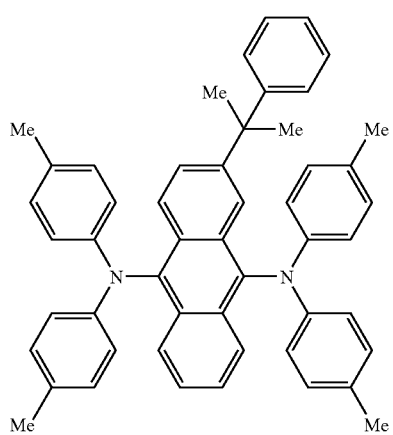
(34)

-continued
(35)
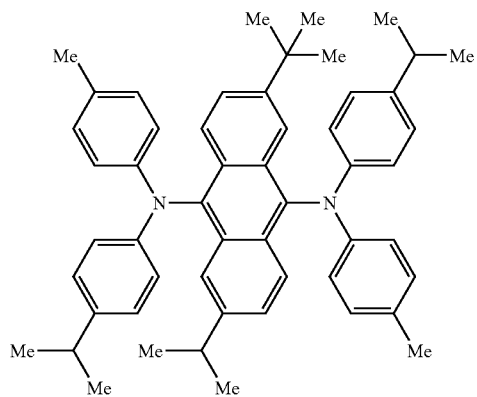
(36)
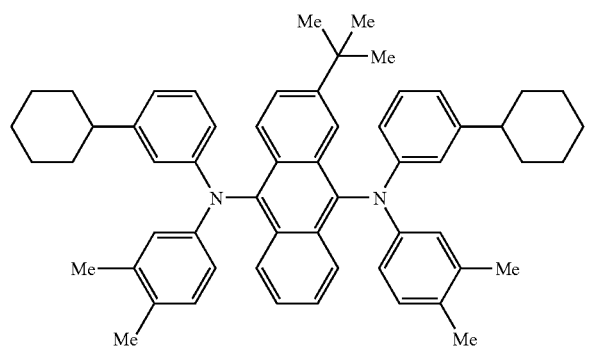
(37)
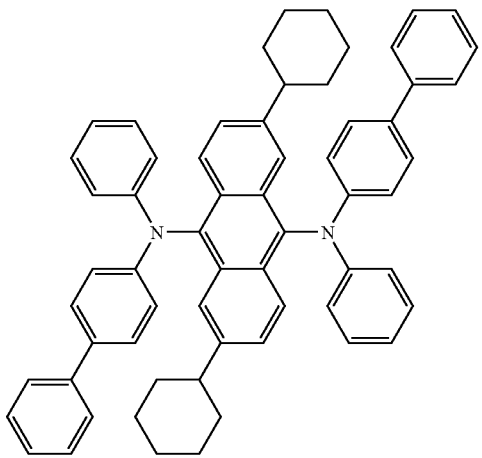

-continued
(38)
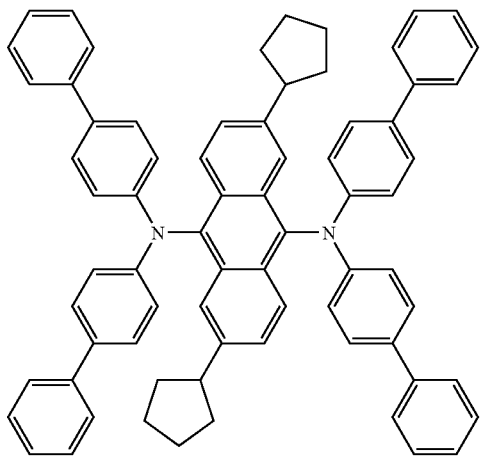
(39)
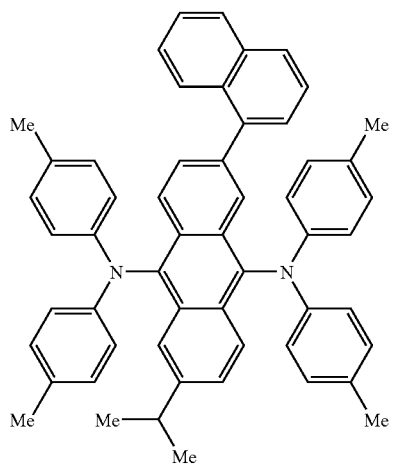
(40)
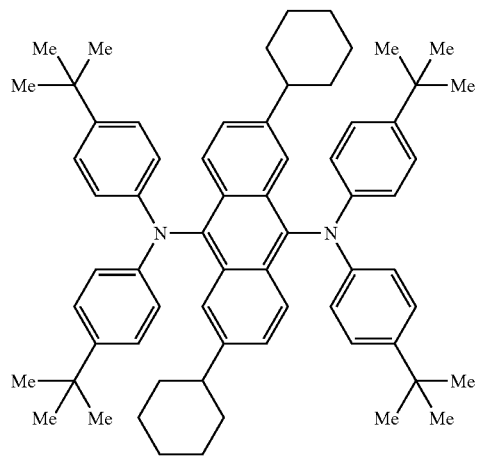

(41)
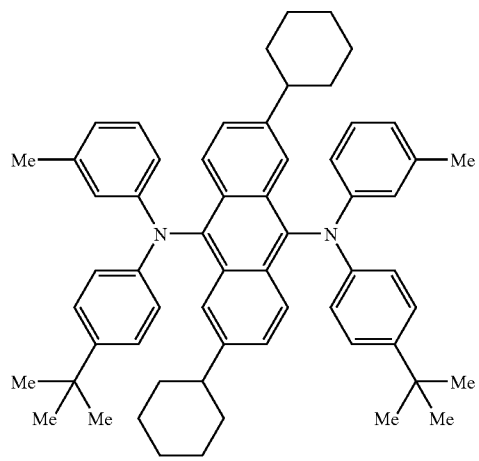
(42)
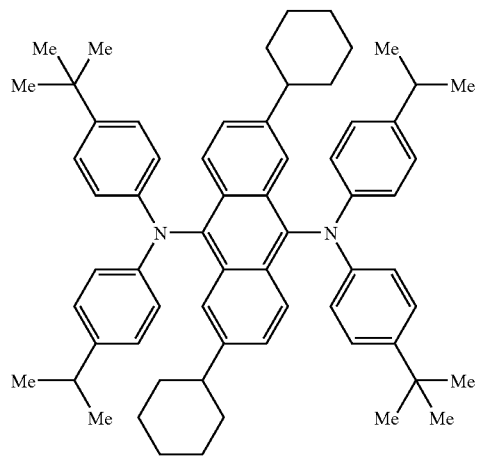
(43)
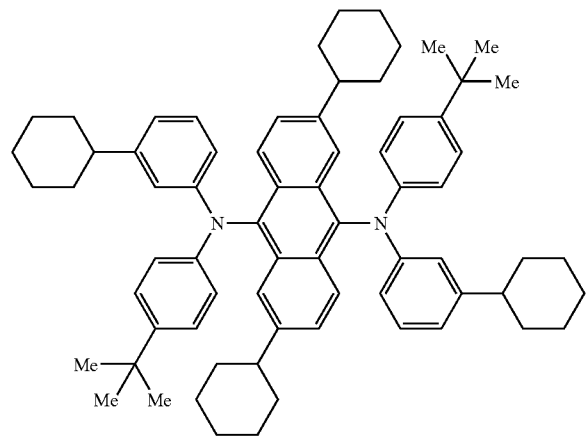

-continued
(44)
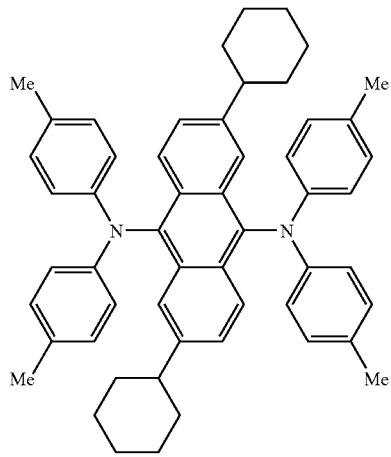
(45)
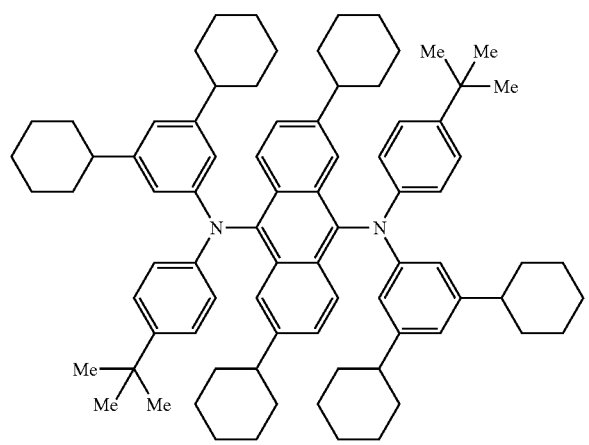
(46)
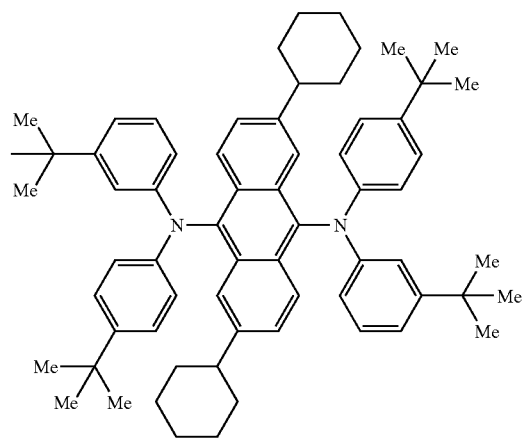

-continued
(47)
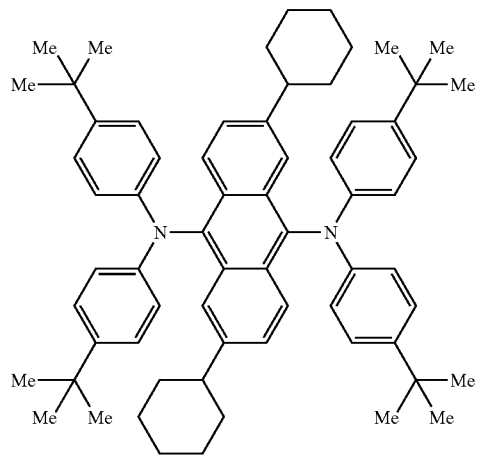
(48)
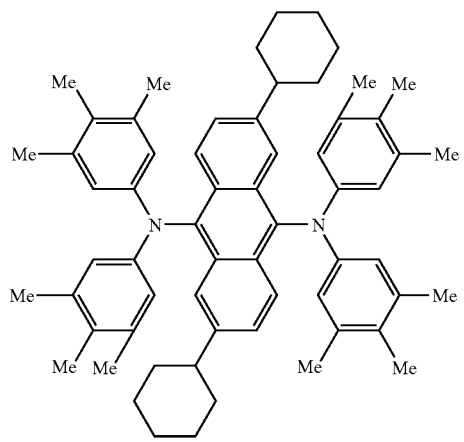
(49)
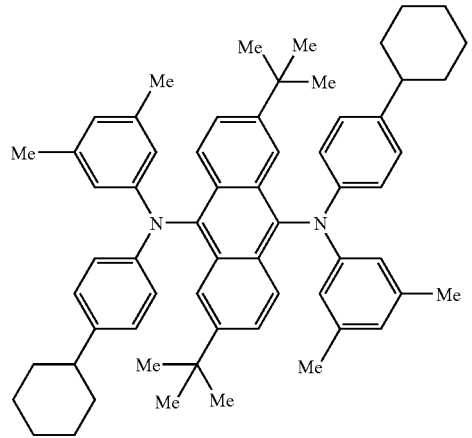

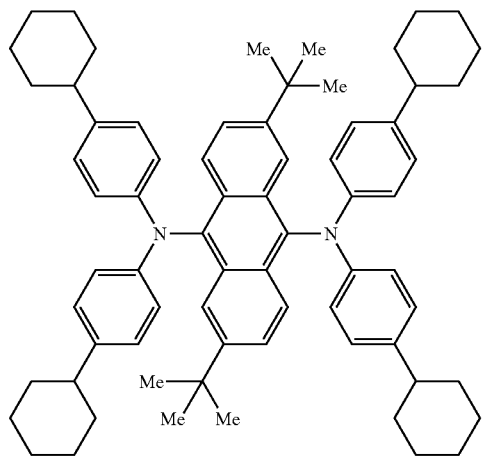
(50)
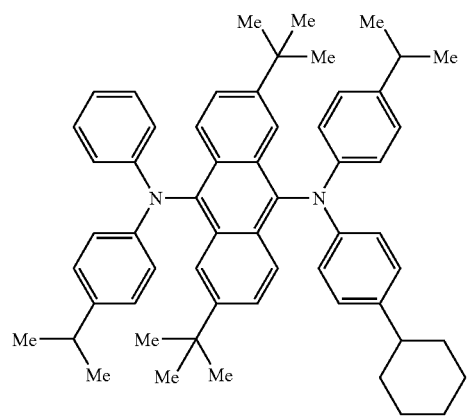
(51)
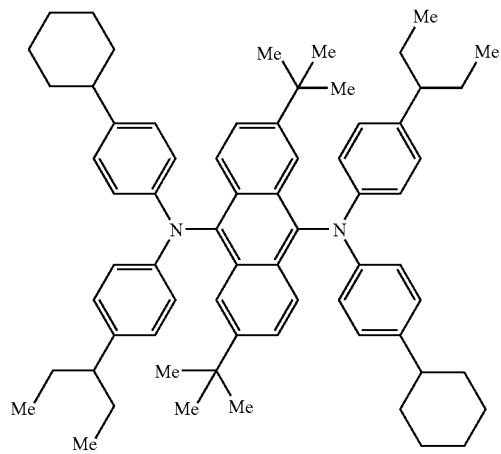
(52)

(53)
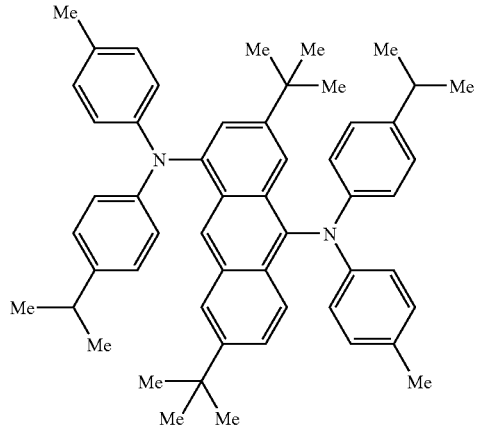
(54)
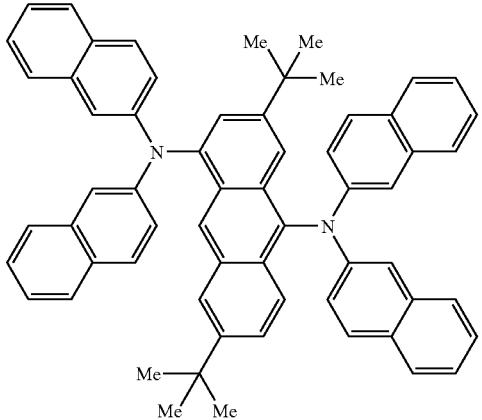
(55)
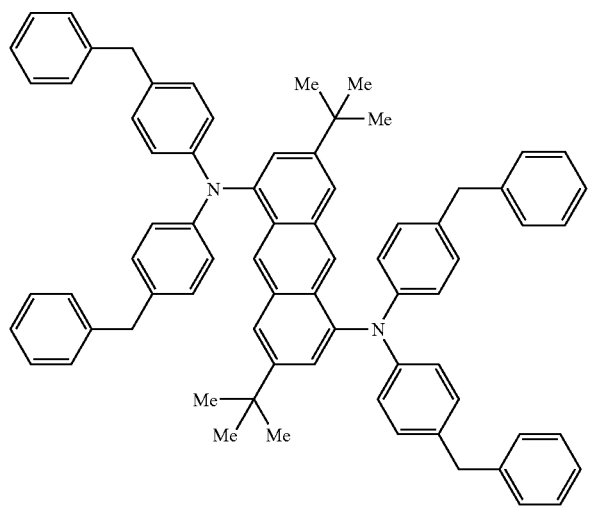

-continued
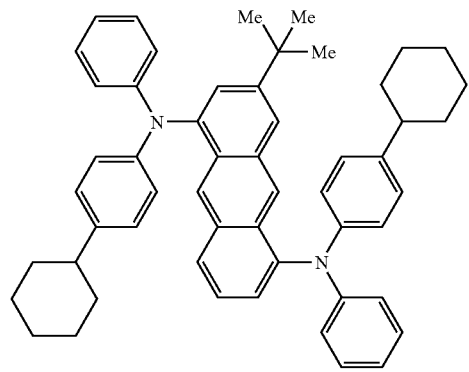
(56)
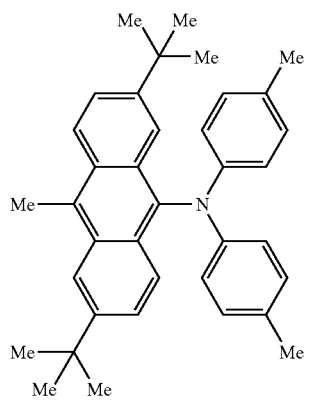
(57)
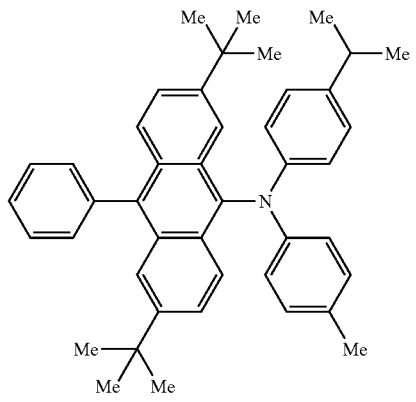
(58)
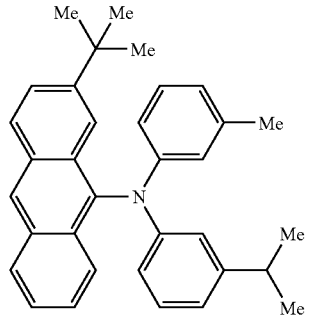
(59)

-continued
(60)
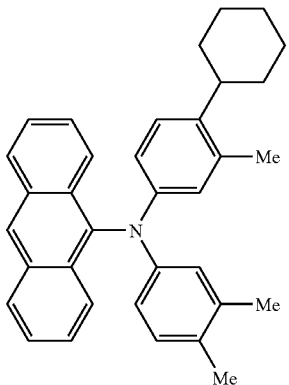
(61)
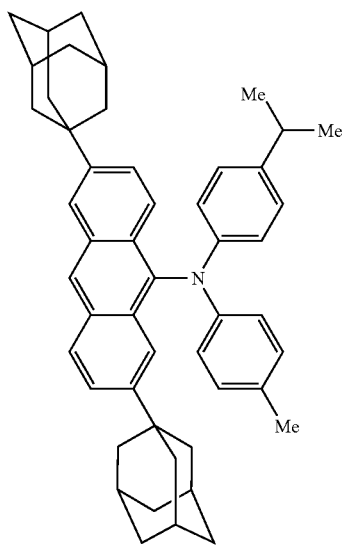
(62)
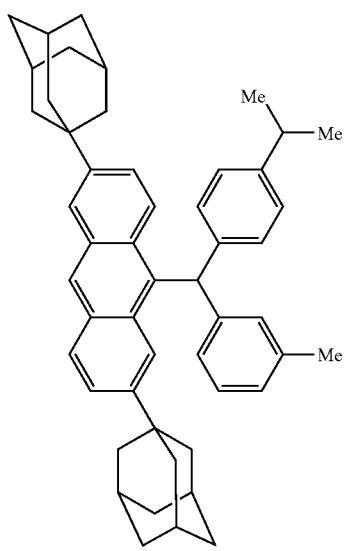

-continued (63)

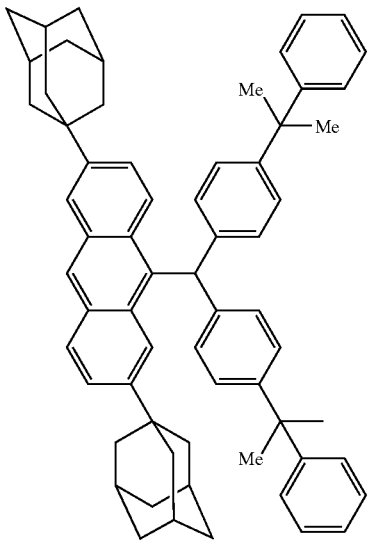

(64)

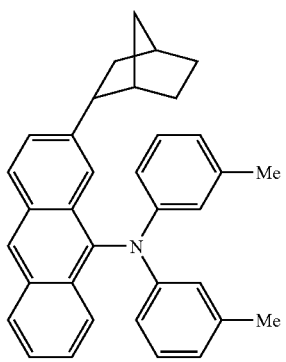

(65)

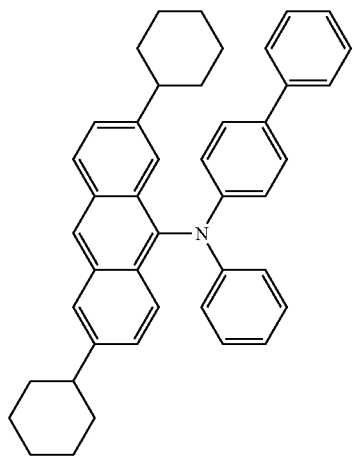

In the aromatic amine derivatives represented by the general formula (1) according to the present invention, since the substituted anthracene structure is bonded to the amine structure substituted with benzene rings having substituent groups, the association between the compounds is prevented, resulting in a prolonged life thereof. In addition, since the anthracene skeleton has bulky substituent groups such as secondary or tertiary alkyl or cycloalkyl groups, the anthracene structure exhibits a large steric repulsion against the amine structure, so that properties of these compounds such as life can be further improved. Further, the aromatic amine derivatives have a strong fluorescence in a solid state, and are excellent in field light emission, which leads to a fluorescent quantum efficiency as high as 0.3 or more. In addition, the aromatic amine derivatives of the present invention exhibit not only excellent capabilities of injecting holes from the metal electrode or organic thin film layers and transporting the holes, but also excellent capabilities of injecting electrons from the metal electrode or organic thin film layers and transporting the electrons, and are, therefore, usefully usable as light emitting materials for organic EL devices. Besides, the aromatic amine derivatives of the present invention may be used together with other hole transporting materials, electron transporting materials or doping materials.

The organic EL device of the present invention includes an anode, a cathode, and one or plural organic thin film layers. In the case of one layer type, a light emitting layer as the organic thin film layer is provided between the anode and cathode. The light emitting layer contains a light emitting material and may further contain a hole injecting material or an electron injecting material in order to effectively transport holes injected from the anode or electrons injected from the cathode to the light emitting material. The aromatic amine derivatives represented by the general formula (1) have a high light emitting property and excellent hole injectability and hole transportability as well as excellent electron injectability and electron transportability and, therefore, can be used as a light emitting material in the light emitting layer.

In the organic EL device of the present invention, the light emitting layer contains the material for organic EL devices according to the present invention in an amount of preferably 0.1 to 20% by weight and more preferably 1 to 10% by weight. Further, the material for organic EL devices according to the present invention exhibits not only an extremely high fluorescent quantum efficiency but also high hole transportability and electron transportability, and further are capable of forming a uniform thin film. Therefore, the light emitting layer may be formed from only the light emitting material of the present invention.

Examples of the organic EL device of a multilayer type include those having multilayer structures such as (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode).

The light emitting layer may also optionally contain, in addition to the compound represented by the general formula (1) according to the present invention, conventionally known materials such as light emitting materials, doping materials, hole injecting materials and electron injecting materials according to requirements. The organic EL device having such a multilayer structure can be prevented from suffering from deterioration in luminance and service life due to quenching. If required, the light emitting materials, doping materials, hole injecting materials and electron injecting materials may be used in combination with each other. The use of the doping materials enables the resultant device to be improved in luminance of light emitted and efficiency of light emission, and further emit a red color light or a blue color light. Further, in the organic EL device of the present invention, the hole injecting layer, the light emitting layer and the electron injecting layer may respectively have a multilayer structure including two or more layers. In this case, the multilayer hole injecting layer may include a hole injecting layer into which holes are injected from the electrode, and a hole transporting layer for accepting the holes from the hole injecting layer and transporting the holes to the light emitting layer. Also, the multi-layer electron injecting layer may include an electron injecting layer into which electrons are injected from the electrode, and an electron transporting layer for accepting the electrons from the electron injecting layer and transporting the electrons to the light emitting layer. These respective layers may be selectively used according to various factors such as energy level of the materials used, heat resistance, and adhesion to the organic thin film layers or the metal electrodes.

Examples of the light emitting materials or doping materials that are usable in the light emitting layer together with the compound represented by the general formula (1) include anthracene, naphthalene, phenanthrene, pyrene, tetracene, coronene, chrysene, fluorescein, perylene, phthaloperylene, naphthaloperylene, perynone, phthaloperynone, naphthaloperynone, diphenyl butadiene, tetraphenyl butadiene, coumarin, oxadiazole, aldazine, bisbenzoxazoline, bisstyryl, pyrazine, cyclopentadiene, quinoline metal complexes, aminoquinoline metal complexes, benzoquinoline metal complexes, imines, diphenyl ethylene, vinyl anthracene, diaminocarbazole, pyran, thiopyran, polymethine, merocyanine, imidazole-chelated oxinoid compounds, quinacridone, rubrene and fluorescent dyes, though not particularly limited thereto.

The hole injecting material is preferably made of compounds which have a good hole transportability as well as excellent capabilities of accepting holes injected from the anode and injecting the holes into the light emitting layer or light emitting material, prevent excited particles (excitons) produced in the light emitting layer from moving into the electron injecting layer or electron injecting material, and exhibit an excellent capability of forming a thin film. Specific examples of the hole injecting material include phthalocyanine derivatives, naphthalocyanine derivatives, porphyrin derivatives, oxazole, oxadiazole, triazole, imidazole, imidazolone, imidazole thione, pyrazoline, pyrazolone, tetrahydroimidazole, hydrazone, acyl hydrazone, polyaryl alkanes, stilbene, butadiene, benzidine-type triphenyl amine, styryl amine-type triphenyl amine, diamine-type triphenyl amine and derivatives thereof, as well as polyvinyl carbazoles, polysilanes, and high molecular materials such as conductive polymers, though not particularly limited thereto.

Of these hole injecting materials usable in the organic EL device of the present invention, more effective hole injecting materials are aromatic tertiary amine derivatives and phthalocyanine derivatives.

Specific examples of the aromatic tertiary amine derivatives include triphenyl amine, tritolyl amine, tolyldiphenyl amine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl cylcohexane, and oligomers and polymers having these aromatic tertiary amine skeletons, though not particularly limited thereto.

Specific examples of the phthalocyanine (Pc) derivatives include phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc and GaPc-O-GaPc, as well as naphthalocyanine derivatives, though not particularly limited thereto.

Also, in the organic EL device of the present invention, a layer containing these aromatic tertiary amine derivatives and/or phthalocyanine derivatives, for example, as the above hole transporting layer or hole injecting layer, is preferably provided between the light emitting layer and the anode.

The electron injecting material is preferably made of compounds which have a good electron transportability as well as excellent capabilities of accepting electrons injected from the cathode and injecting the electrons into the light emitting layer or light emitting material, prevent excited particles produced in the light emitting layer from moving into the hole injecting layer, and exhibit an excellent capability of forming a thin film. Specific examples of the electron injecting material include fluorenone, anthraquinodimethane, diphenoquinone, thiopyran dioxide, oxazole, oxadiazole, triazole, imidazole, perylenetetracarboxylic acid, fluorenylidene methane, anthrone, and derivatives thereof, though not particularly limited thereto. Further, an electron accepting substance and an electron donating substance may be added to the hole injecting material and the electron injecting material, respectively, for enhancing a sensitization thereof.

In the organic EL device of the present invention, among these electron injecting materials, more effective electron injecting materials are metal complex compounds and nitrogen-containing five-membered ring derivatives.

Specific examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, and bis(2-methyl-8-quinolinato) (2-naphtholato) gallium, though not particularly limited thereto.

The preferred nitrogen-containing five membered ring derivatives are, for example, derivatives of oxazole, thiazole, oxadiazole, thiadiazole or triazole. Specific examples of the nitrogen-containing five membered ring derivatives include 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4''-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4''-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4''-biphenyl)-1,3,4-triazole, 2,5-bis(1-naphthyl)-1,3,4-triazole, and 1,4-bis[2-(5-phenyltriazolyl)]benzene, though not particularly limited thereto.

In the organic EL device of the present invention, the light emitting layer may also optionally contain, in addition to the compound represented by the general formula (1), at least one material selected from the group consisting of light emitting materials, doping materials, hole injecting materials and electron injecting materials. The organic EL device of the present invention may be further provided on a surface thereof with a protective layer, or the whole part thereof may be protected with silicone oil, resins, etc., in order to enhance a stability thereof against temperature, humidity, atmosphere, etc.

The anode of the organic EL device according to the present invention may be suitably made of a conductive material having a work function more than 4 eV. Examples of the conductive material for the anode include carbon, aluminum, vanadium, iron, cobalt, nickel, tungsten, silver, gold, platinum, palladium and alloys thereof, metal oxides such as tin oxide and indium oxide which are used for ITO substrates or NESA substrates, and organic conductive resins such as polythiophene and polypyrrole. The cathode of the organic EL device according to the present invention may be suitably made of a conductive material having a work function of 4 eV or less. Examples of the conductive material for the cathode include magnesium, calcium, tin, lead, titanium, yttrium, lithium, ruthenium, manganese, aluminum, lithium fluoride and alloys thereof, though not particularly limited thereto. Typical examples of the alloys include alloys of magnesium and silver, alloys of magnesium and indium, and alloys of lithium and aluminum, though not particularly limited thereto. The ratio between the constituting metals in the alloys may be controlled and appropriately determined depending upon temperature of vapor deposition sources, atmosphere, vacuum degree, etc. The anode and cathode may be constituted of two or more layers, if required.

At least one surface of the organic EL device of the present invention preferably exhibits a sufficient transparency in a wavelength range of light emitted therefrom in order to enhance an efficiency of light emission thereof. Further, the substrate used in the device is also preferably transparent. The transparent electrode is formed from the above conductive material by vapor deposition method, sputtering method, etc., so as to ensure a desirable transparency thereof. The electrode disposed on a light emitting surface of the device preferably has a light transmittance of 10% or more. The substrate is not particularly limited as long as it has a good mechanical and thermal strength as well as a good transparency. Examples of the substrate include glass substrates and transparent resin films. Specific examples of the transparent resin films include films made of polyethylene, ethylene-vinyl acetate copolymer, ethylene-vinyl alcohol copolymer, polypropylene, polystyrene, polymethyl methacrylate, polyvinyl chloride, polyvinyl alcohol, polyvinyl butyral, nylons, polyether ether ketones, polysulfones, polyether sulfones, tetrafluoroethylene-perfluoroalkylvinyl ether copolymer, polyvinyl fluoride, tetrafluoroethylene-ethylene copolymer, tetrafluororethylene-hexafluoropropylene copolymer, polychlorotrifluoroethylene, polyvinylidene fluoride, polyesters, polycarbonates, polyurethanes, polyimides, and polyether imides.

The respective layers of the organic EL device of the present invention may be formed by either a dry film-forming method such as vacuum deposition, sputtering, plasma and ion-plating, or a wet film-forming method such as spin-coating, dipping and flow-coating. The thickness of the respective layers is not particularly limited, but should be adjusted to an appropriate range. If the thickness is too large, a large electric voltage must be applied to the device in order to achieve a desired light output, resulting in a poor efficiency of light emission. On the other hand, if the thickness is too small, pinholes tend to be formed in the layers, thereby failing to obtain a sufficient luminance of light emitted even upon applying an electric field thereto. The suitable thickness of the respective layers is usually in the range of from 5 nm to 10 μm and preferably from 10 nm to 0.2 μm.

In the wet film-forming method, materials constituting the respective layers are dissolved or dispersed in a suitable solvent such as ethanol, chloroform, tetrahydrofuran and dioxane to form a thin film thereof. The solvent used for forming the respective layers is not particularly limited. Also, suitable resins or additives may be added to the respective organic thin film layers for the purposes of improving a film-forming property, preventing formation of pinholes in the resultant film, etc. Examples of the resins usable for the above purposes include insulating resins such as polystyrene, polycarbonates, polyarylates, polyesters, polyamides, polyurethanes, polysulfones, polymethyl methacrylate, polymethyl acrylate and celluloses as well as copolymers thereof, photoconductive resins such as poly-N-vinyl carbazole and polysilanes, and conductive resins such as polythiophene and polypyrrole. Examples of the additives include antioxidants, ultraviolet absorbers and plasticizers.

As described above, by using the aromatic amine derivative of the present invention in organic thin film layers of the organic EL device, the obtained organic EL device can exhibit a long life and a high luminance of light emitted and a high efficiency of light emission.

The organic EL device of the present invention is suitably applied to, for example, surface light-emitting members such as a flat panel display for wall-type TV, light sources for copiers, printers, back light for liquid crystal displays and measuring equipments, display panels, marker lights, etc. Further, the material of the present invention can be used not only for organic EL devices but also in other applications such as electrophotographic members, photoelectric converters, solar cells, image sensors, etc.

The present invention will be described in more detail by reference to the following examples. However, it should be noted that these examples are only illustrative and not intended to limit the invention thereto.

SYNTHESIS EXAMPLE 1

Synthesis of Compound (6)

Under an argon flow, 6.0 g (10 mmol) of 2,6-di(1-adamantyl)anthracene, 5.6 g (25 mmol) of 4-isopropylphenyl-p-tolylamine, 0.03 g (1.5 mol %) of palladium acetate, 0.06 g (3 mol %) of tri-t-butyl phosphine, 2.4 g (25 mmol) of t-butoxy sodium and 100 mL of dried toluene were charged into a 300 mL three-necked flask equipped with a condenser tube, and then stirred under heating at 100° C. over night. After completion of the reaction, the precipitated crystals were separated from the reaction solution by filtration, and then washed with 50 mL of toluene and 100 mL of methanol, thereby obtaining 7.2 g of a light-yellow powder. The thus obtained powder was subjected to NMR spectrum analysis (FIG. 1) and FD-MS (field desorption mass spectrum analysis). As a result, the reaction product was identified as the compound (6) (yield: 82%).

Meanwhile, the NMR spectrum was measured by Fourier-transform NMR analyzer "R-1900" (90 MHz) available from Hitachi Limited, using $CDCl_3$ as a solvent.

SYNTHESIS EXAMPLE 2

Synthesis of Compound (7)

Figure 2:
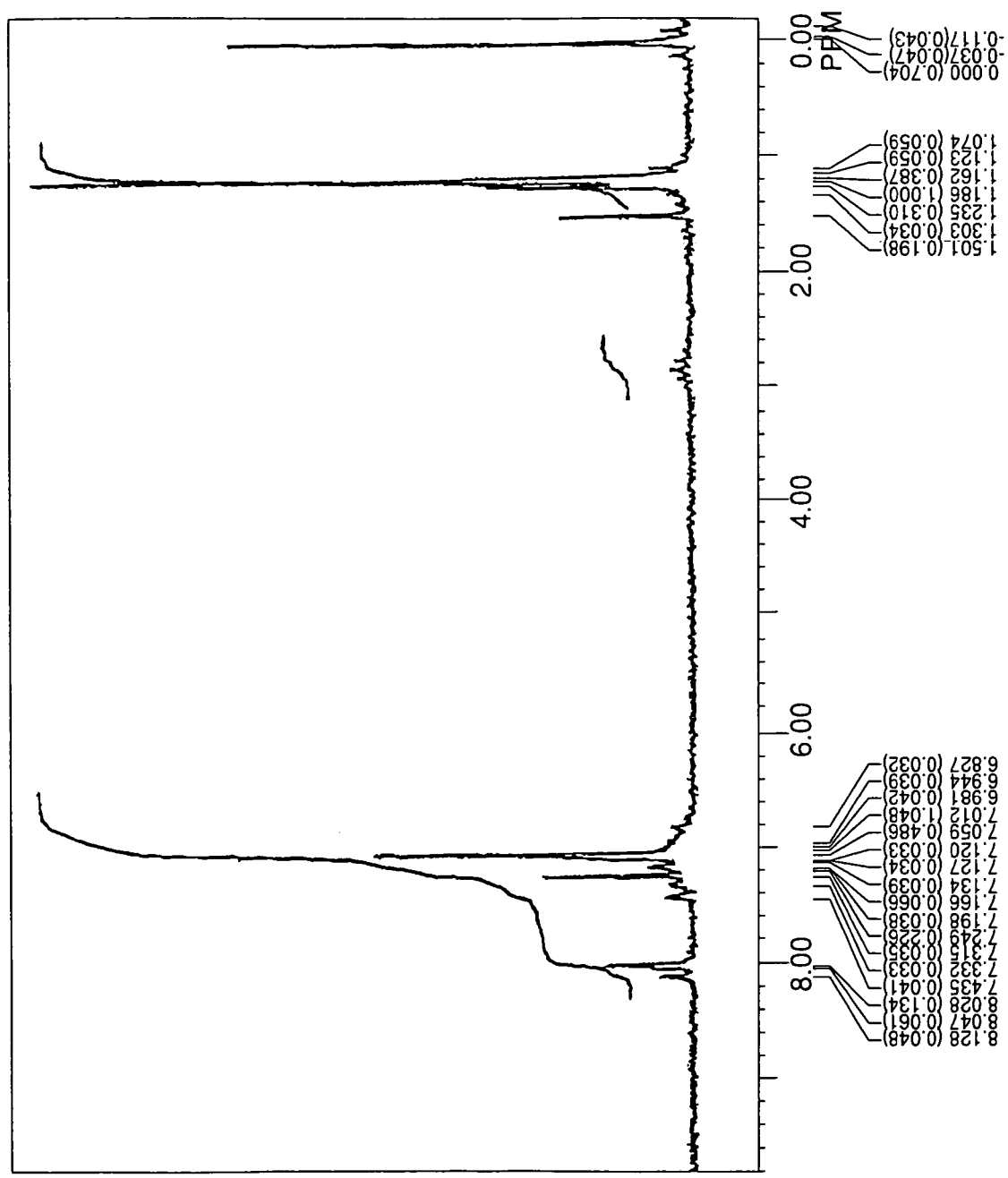
FIG. 2 is a view showing NMR spectrum of the compound (7) as an example of the aromatic amine derivatives of the present invention.

Under an argon flow, 4.5 g (10 mmol) of 2,6-di-t-butyl anthracene, 5.2 g (25 mmol) of 4-isobutyl diphenyl amine, 0.03 g (1.5 mol %) of palladium acetate, 0.06 g (3 mol %) of tri-t-butyl phosphine, 2.4 g (25 mmol) of t-butoxy sodium and 100 mL of dried toluene were charged into a 300 mL three-necked flask equipped with a condenser tube, and then stirred under heating at 100° C. over night. After completion of the reaction, the precipitated crystals were separated from the reaction solution by filtration, and then washed with 50 mL of toluene and 100 mL of methanol, thereby obtaining 6.0 g of a light-yellow powder. The thus obtained powder was subjected to NMR spectrum analysis (FIG. 2) and FD-MS. As a result, the reaction product was identified as the compound (7) (yield: 85%). Meanwhile, the NMR spectrum was measured under the same conditions as described in SYNTHESIS EXAMPLE 1.

SYNTHESIS EXAMPLE 3

Synthesis of Compound (8)

Figure 3:
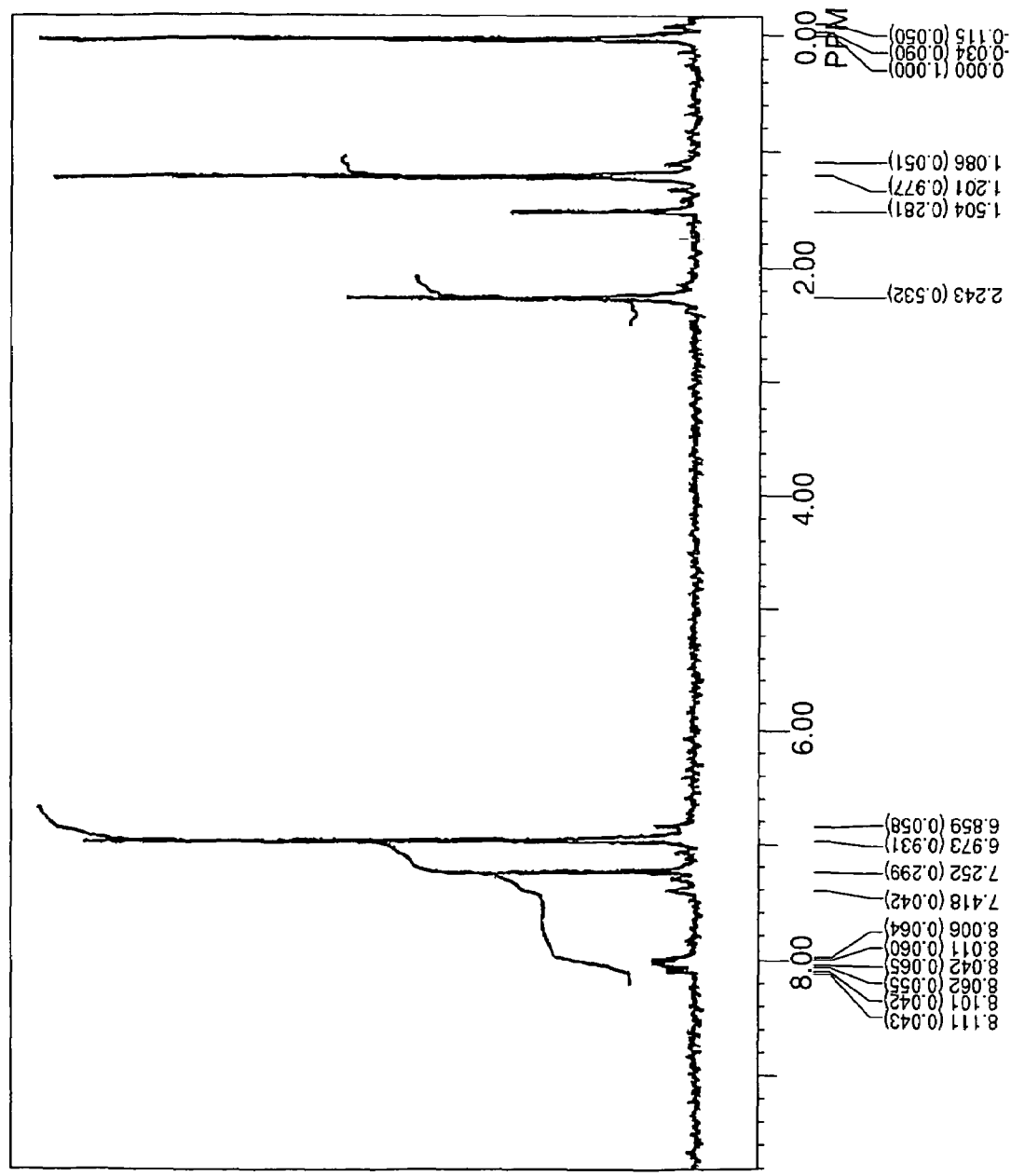
FIG. 3 is a view showing NMR spectrum of the compound (8) as an example of the aromatic amine derivatives of the present invention.

Under an argon flow, 4.5 g (10 mmol) of 2,6-di-t-butyl anthracene, 4.9 g (25 mmol) of p,p'-ditolylamine, 0.03 g (1.5 mol %) of palladium acetate, 0.06 g (3 mol %) of tri-t-butyl phosphine, 2.4 g (25 mmol) of t-butoxy sodium and 100 mL of dried toluene were charged into a 300 mL three-necked flask equipped with a condenser tube, and then stirred under heating at 100° C. over night. After completion of the reaction, the precipitated crystals were separated from the reaction solution by filtration, and then washed with 50 mL of toluene and 100 mL of methanol, thereby obtaining 6.3 g of a light-yellow powder. The thus obtained powder was subjected to NMR spectrum analysis (FIG. 3) and FD-MS. As a result, the reaction product was identified as the compound (8) (yield: 93%). Meanwhile, the NMR spectrum was measured under the same conditions as described in SYNTHESIS EXAMPLE 1.

SYNTHESIS EXAMPLE 4

Synthesis of Compound (9)

Figure 4:
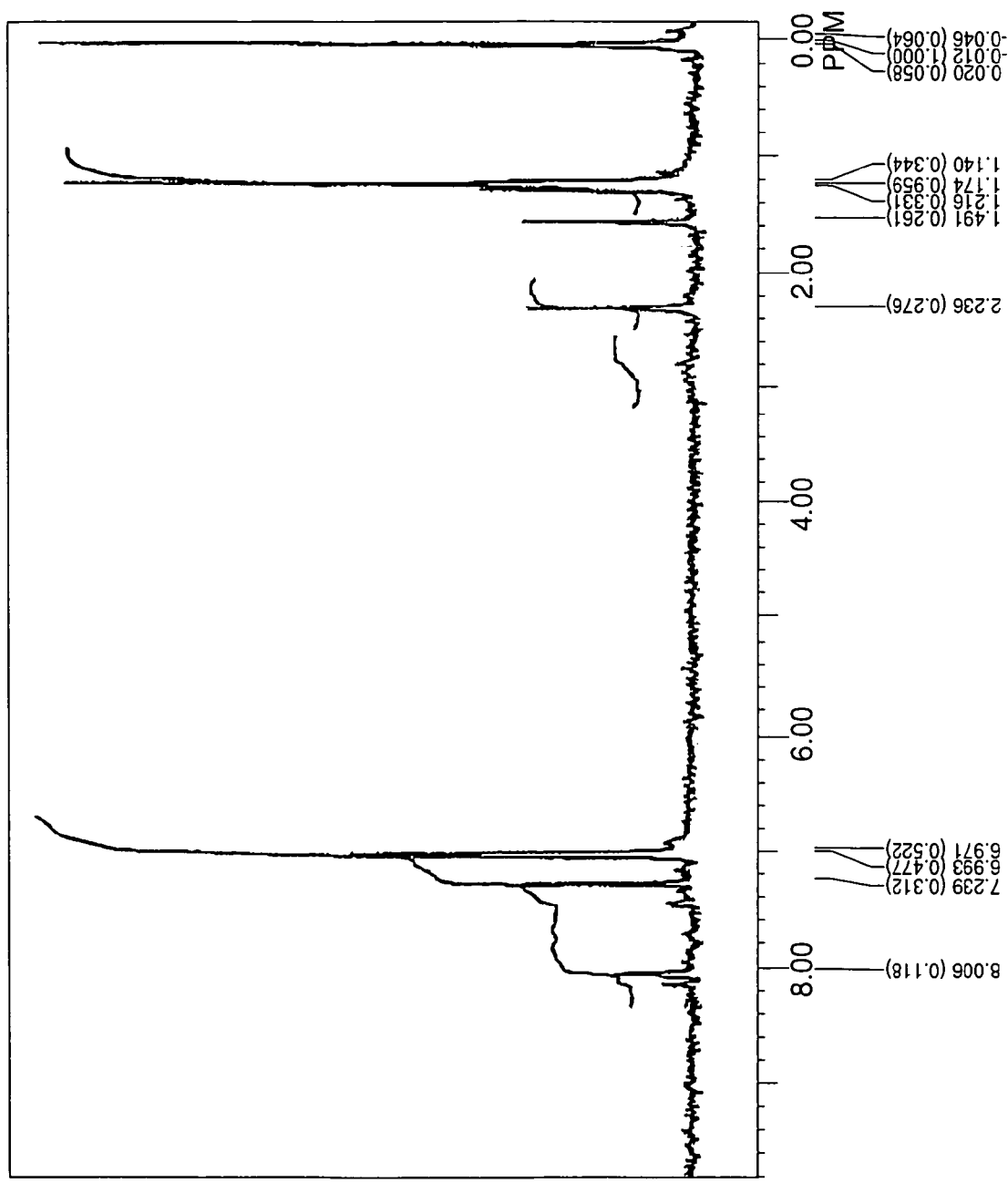
FIG. 4 is a view showing NMR spectrum of the compound (9) as an example of the aromatic amine derivatives of the present invention.

Under an argon flow, 4.5 g (10 mmol) of 2,6-di-t-butyl anthracene, 5.6 g (25 mmol) of 4-isopropylphenyl-p-tolylamine, 0.03 g (1.5 mol %) of palladium acetate, 0.06 g (3 mol %) of tri-t-butyl phosphine, 2.4 g (25 mmol) of t-butoxy sodium and 100 mL of dried toluene were charged into a 300 mL three-necked flask equipped with a condenser tube, and then stirred under heating at 100° C. over night. After completion of the reaction, the precipitated crystals were separated from the reaction solution by filtration, and then washed with 50 mL of toluene and 100 mL of methanol, thereby obtaining 7.0 g of a light-yellow powder. The thus obtained powder was subjected to NMR spectrum analysis (FIG. 4) and FD-MS. As a result, the reaction product was identified as the compound (9) (yield: 95%). Meanwhile, the NMR spectrum was measured under the same conditions as described in SYNTHESIS EXAMPLE 1.

SYNTHESIS EXAMPLE 5

Synthesis of Compound (10)

Figure 5:
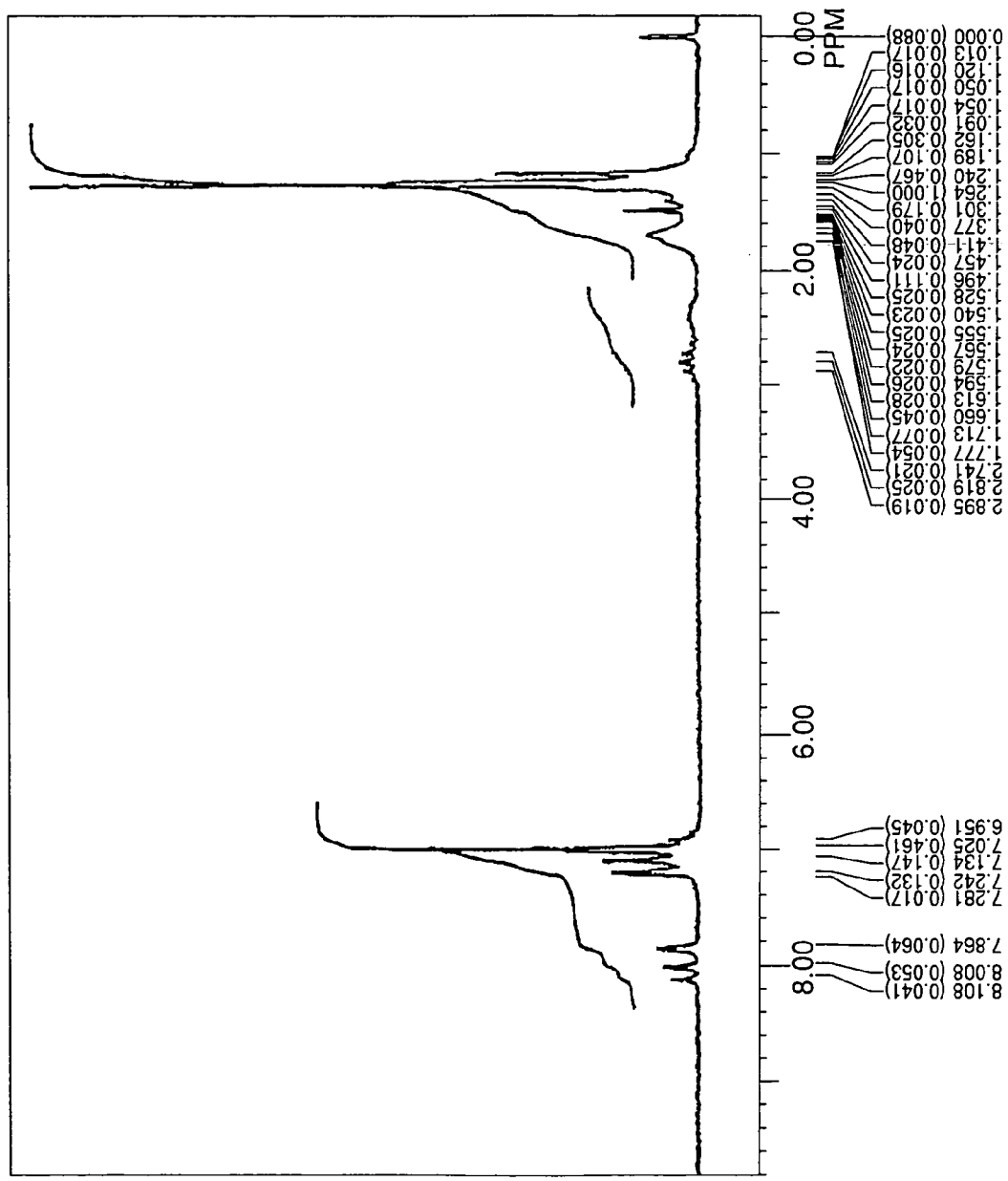
FIG. 5 is a view showing NMR spectrum of the compound (10) as an example of the aromatic amine derivatives of the present invention.

Under an argon flow, 5.0 g (10 mmol) of 2.6-dicyclohexyl anthracene, 5.6 g (25 mmol) of 4-isopropylphenyl-p-tolylamine, 0.03 g (1.5 mol %) of palladium acetate, 0.06 g (3 mol %) of tri-t-butyl phosphine, 2.4 g (25 mmol) of t-butoxy sodium and 100 mL of dried toluene were charged into a 300 mL three-necked flask equipped with a condenser tube, and then stirred under heating at 100° C. over night. After completion of the reaction, the precipitated crystals were separated from the reaction solution by filtration, and then washed with 50 mL of toluene and 100 mL of methanol, thereby obtaining 7.1 g of a light-yellow powder. The thus obtained powder was subjected to NMR spectrum analysis (FIG. 5) and FD-MS. As a result, the reaction product was identified as the compound (10) (yield: 90%). Meanwhile, the NMR spectrum was measured under the same conditions as described in SYNTHESIS EXAMPLE 1.

SYNTHESIS EXAMPLE 6

Synthesis of Compound (11)

Figure 6:
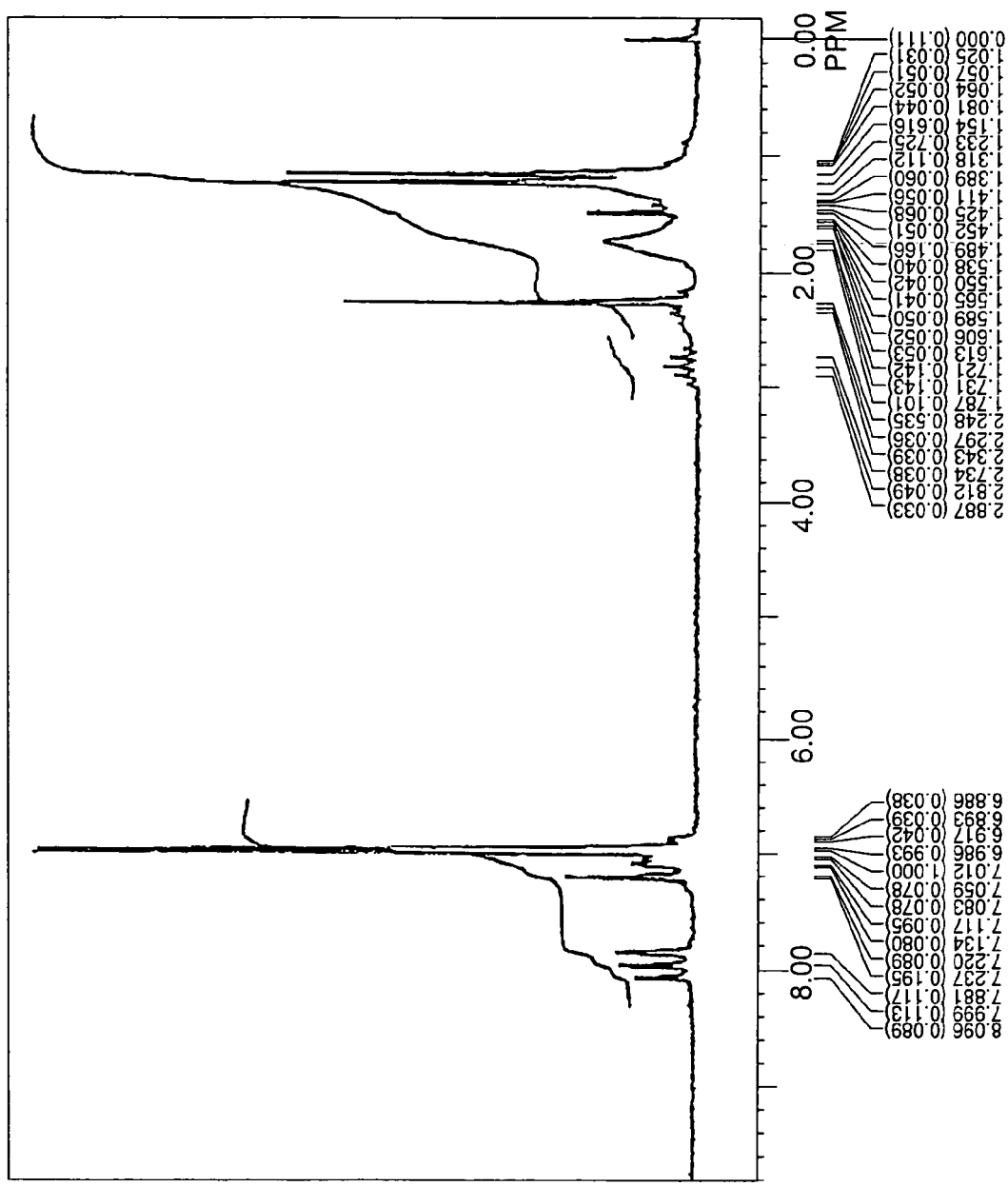
FIG. 6 is a view showing NMR spectrum of the compound (11) as an example of the aromatic amine derivatives of the present invention.

Under an argon flow, 5.0 g (10 mmol) of 2.6-dicyclohexyl anthracene, 6.7 g (25 mmol) of 4-t-butylphenyl-4-isopropylphenyl amine, 0.03 g (1.5 mol %) of palladium acetate, 0.06 g (3 mol %) of tri-t-butyl phosphine, 2.4 g (25 mmol) of t-butoxy sodium and 100 mL of dried toluene were charged into a 300 mL three-necked flask equipped with a condenser tube, and then stirred under heating at 100° C. over night. After completion of the reaction, the precipitated crystals were separated from the reaction solution by filtration, and then washed with 50 mL of toluene and 100 mL of methanol, thereby obtaining 8.3 g of a light-yellow powder. The thus obtained powder was subjected to NMR spectrum analysis (FIG. 6) and FD-MS. As a result, the reaction product was identified as the compound (11) (yield: 95%). Meanwhile, the NMR spectrum was measured under the same conditions as described in SYNTHESIS EXAMPLE 1.

EXAMPLE 1

A 120 nm-thick transparent electrode made of indium oxide was formed on a glass substrate having a size of 25 mm×75 mm×1.1 mm. The glass substrate with the transparent electrode was cleaned by irradiation of UV and ozone, and then mounted to a vacuum vapor deposition apparatus.

First, N',N"-bis[4-(diphenylamino)phenyl]-N',N"-diphenylbiphenyl-4,4'-diamine was vapor-deposited to form a hole injecting layer having a thickness of 60 nm, and then N,N,N',N'-tetrakis(4-biphenyl)-4,4'-benzidine was vapor-deposited on the hole injecting layer to form a hole transporting layer having a thickness of 20 nm. Then, 10,10'-bis[1,1',4',1"]terphenyl-2-yl-9,9'-bianthracenyl and the above compound (6) were simultaneously vapor-deposited at a weight ratio of 40:3 on the hole transporting layer to form a light emitting layer having a thickness of 40 nm.

Next, tris(8-hydroxyquinolinato)aluminum was vapor-deposited on the light emitting layer to form an electron injecting layer having a thickness of 20 nm. Then, lithium fluoride and then aluminum were successively vapor-deposited on the electron injecting layer to form layers having thicknesses of 1 nm and 150 nm, respectively. The thus formed lithium fluoride/aluminum film was functioned as a cathode. As a result, an organic EL device was produced.

When the thus obtained organic EL device was subjected to energizing test, it was confirmed that a green light with an efficiency of light emission of 20 cd/A and a luminance of light emission of 2011 cd/m$^2$ (light emission maximum wavelength: 530 nm) was emitted at a voltage of 7.0 V and a current density of 10 mA/cm$^2$. Further, as a result of subjecting the device to a D.C. continuous energizing test at an initial luminance of 3000 cd/m$^2$, it was confirmed that the half life thereof was 4500 h.

EXAMPLE 2

The same procedure as in EXAMPLE 1 was repeated except for using the compound (9) in place of the compound (6), thereby producing an organic EL device.

When the thus obtained organic EL device was subjected to energizing test, it was confirmed that a green light with an efficiency of light emission of 19 cd/A and a luminance of light emission of 1914 cd/m$^2$ (light emission maximum wavelength: 527 nm) was emitted at a voltage of 7.5 V and a current density of 10 mA/cm$^2$. Further, as a result of subjecting the device to a D.C. continuous energizing test by the same method as described in EXAMPLE 1, it was confirmed that the half life thereof was 4000 h.

EXAMPLE 3

The same procedure as in EXAMPLE 1 was repeated except for using the compound (10) in place of the compound (6), thereby producing an organic EL device.

When the thus obtained organic EL device was subjected to energizing test, it was confirmed that a green light with an efficiency of light emission of 22 cd/A and a luminance of light emission of 2201 cd/m$^2$ (light emission maximum wavelength: 529 nm) was emitted at a voltage of 7.0 V and a current density of 10 mA/cm$^2$. Further, as a result of subjecting the device to a D.C. continuous energizing test by the same method as described in EXAMPLE 1, it was confirmed that the half life thereof was 5000 h.

EXAMPLE 4

The same procedure as in EXAMPLE 1 was repeated except for using the compound (11) in place of the compound (6), thereby producing an organic EL device.

When the thus obtained organic EL device was subjected to energizing test, it was confirmed that a green light with an efficiency of light emission of 24 cd/A and a luminance of light emission of 2411 cd/m$^2$ (light emission maximum wavelength: 529 nm) was emitted at a voltage of 7.0 V and a current density of 10 mA/cm$^2$. Further, as a result of subjecting the device to a D.C. continuous energizing test by the same method as described in EXAMPLE 1, it was confirmed that the half life thereof was 6000 h.

COMPARATIVE EXAMPLE 1

The same procedure as in EXAMPLE 1 was repeated except for using 9,10-bis(diphenylamino)anthracene in place of the compound (6), thereby producing an organic EL device.

When the thus obtained organic EL device was subjected to energizing test, it was confirmed that a yellow light with an efficiency of light emission of 9 cd/A and a luminance of light emission of 987 cd/m$^2$ (light emission maximum wavelength: 555 nm) was emitted at a voltage of 6.8 V and a current density of 10 mA/cm$^2$. Further, as a result of subjecting the device to a D.C. continuous energizing test by the same method as described in EXAMPLE 1, it was confirmed that the half life thereof was as short as 1500 h.

COMPARATIVE EXAMPLE 2

The same procedure as in EXAMPLE 1 was repeated except for using 2-methyl-9,10-bis(diphenylamino)anthracene in place of the compound (6), thereby producing an organic EL device.

When the thus obtained organic EL device was subjected to energizing test, it was confirmed that a yellow light with an efficiency of light emission of 8 cd/A and a luminance of light emission of 805 cd/m$^2$ (light emission maximum wavelength: 558 nm) was emitted at a voltage of 6.8 V and a current density of 10 mA/cm$^2$. Further, as a result of subjecting the device to a D.C. continuous energizing test by the same method as described in EXAMPLE 1, it was confirmed that the half life thereof was as short as 700 h.

INDUSTRIAL APPLICABILITY

The organic EL device produced using the novel aromatic amine derivative as a light emitting material according to the present invention can exhibit a practically sufficient luminance of light emitted even upon applying a low voltage thereto, and has a high efficiency of light emission, and is free from deterioration in properties even after being used for a long period of time and, therefore, has a long life. Therefore, the organic EL device of the present invention has a high utility and is extremely useful as a light source for various electronic equipments.

The invention claimed is:

1. The aromatic amine derivative represented by the following general formula (2):

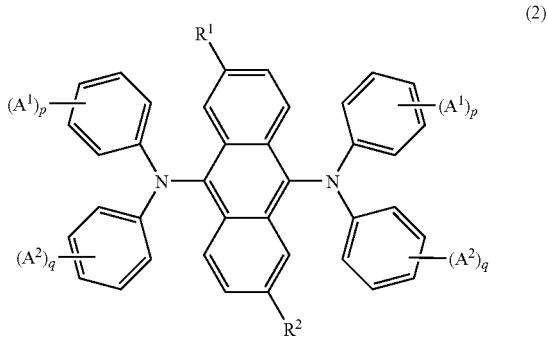

(2)

wherein $A^1$ and $A^2$ are each independently a hydrogen atom, a substituted or unsubstituted alkyl group having 1 to 10 carbon atoms, a substituted or unsubstituted aryl group having 5 to 50 nuclear carbon atoms, a substituted or unsubstituted cycloalkyl group having 3 to 20 nuclear carbon atoms, a substituted or unsubstituted alkoxy group having 1 to 10 carbon atoms, a substituted or unsubstituted aryloxy group having 5 to 50 nuclear carbon atoms, a substituted or unsubstituted arylamino group having 5 to 50 nuclear carbon atoms, a substituted or unsubstituted alkylamino group having 1 to 10 carbon atoms, or a halogen atom, with the proviso that $A^1$ and $A^2$ are not both hydrogen atoms, p and q are each an integer of 1 to 5, and when p or q is 2 or more, a plurality of $A^1$ or $A^2$ groups may be the same or different and may be bonded to each other to form a saturated or unsaturated ring;

$R^1$ is a substituted or unsubstituted secondary or tertiary alkyl group having 3 to 10 carbon atoms, or a subsituted or unsubstituted secondary or tertiary cycloalkyl group having 3 to 10 carbon atoms;

$R^2$ is a substituted or unsubstituted alkyl group having 1 to 10 carbon atoms, a substituted or unsubstituted aryl group having 5 to 50 nuclear carbon atoms, a substituted or unsubstituted cycloalkyl group having 3 to 20 nuclear carbon atoms, a substituted or unsubstituted alkoxy group having 1 to 10 carbon atoms, a substituted or unsubstituted aryloxy group having 5 to 50 nucelar carbon atoms, a substituted or unsubstituted arylamino group having 5 to 50 nuclear carbon atoms, a substituted or unsubstituted alkylamino group having 1 to 10 carbon atoms, or a halogen atom.

2. The aromatic amine derivative according to claim 1, wherein said aromatic amine derivative is represented by the following general formula (2-1):

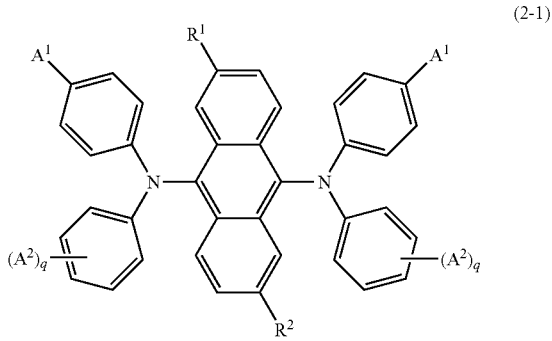

(2-1)

wherein $A^1$, $A^2$, $R^1$ and $R^2$ are the same as defined above.

3. The aromatic amine derivative according to claim 1, wherein said aromatic amine derivative is represented by the following general formula (2-2):

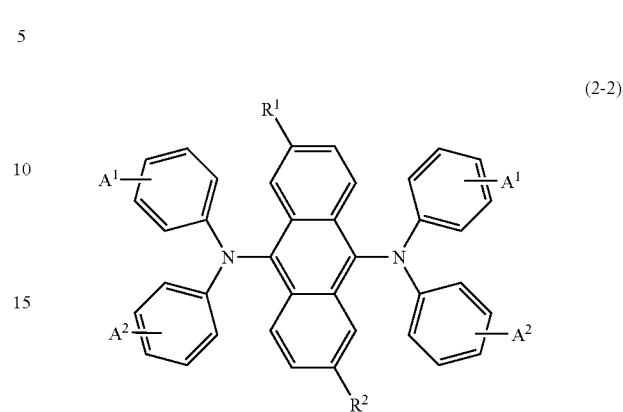

(2-2)

wherein $A^1$, $A^2$, $R^1$ and $R^2$ are the same as defined above.

4. The aromatic amine derivative according to claim 2, wherein said aromatic amine derivative is represented by the following general formula (2-3):

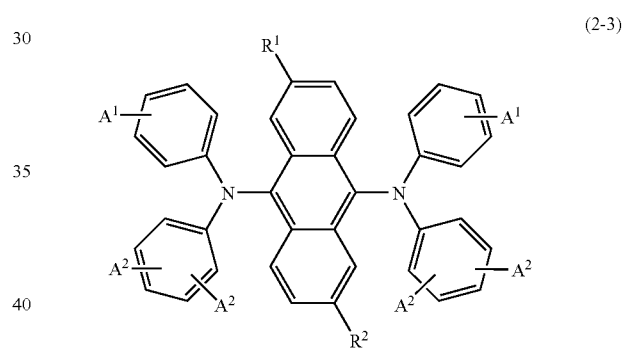

(2-3)

wherein $A^1$, $A^2$, $R^1$ and $R^2$ are the same as defined above.

5. An organic electroluminescence device comprising a cathode, an anode and one or plural organic thin film layers having at least a light emitting layer which are sandwiched between the cathode and the anode, wherein at least one of the organic thin film layers contains the aromatic amine derivative as claimed in claim 1 in the form of a single substance or a component of a mixture.

6. The organic electroluminescence device according to claim 5, wherein the light emitting layer contains the aromatic amine derivative.

7. The aromatic amine derivative according to claim 1, wherein at least one of $A^1$ and $A^2$ is a substituted or unsubstituted alkyl group having 1 to 10 carbon atoms, a substituted or unsubstituted aryl group having 5 to 50 nuclear carbon atoms, a substituted or unsubstituted cycloalkyl group having 3 to 20 nuclear carbon atoms, a substituted or unsubstituted alkoxy group having 1 to 10 carbon atoms, a substituted or unsubstituted aryloxy group having 5 to 50 nuclear carbon atoms, a substituted or unsubstituted arylamino group having 5 to 50 nuclear carbon atoms, a substituted or unsubstituted alkylamino group having 1 to 10 carbon atoms, or a halogen atom; p and q are each an integer of 1 to 5 and s is an integer of 1 to 9 wherein when p or q is 2 or more, a plurality of $A^1$ or $A^1$ groups may be the same or different and may be bonded to each other to form an saturated or unsaturated ring, with the proviso that both of $A^1$ and $A^2$ are not simultaneously hydrogen atoms.

8. The aromatic amine derivative according to claim 1, wherein $R^2$ is a substituted or unsubstituted propyl group, a substituted or unsubstituted butyl group, a substituted or unsubstituted cyclopentyl group, or a substituted or unsubstituted cyclohexyl group.

9. The aromatic amine derivative according to claim 1, wherein $R^1$ is a cyclopentyl, cyclohexyl, norbornyl or adamantyl group.

* * * * *